United States Patent [19]

Hjertén et al.

[11] Patent Number: 5,645,717
[45] Date of Patent: Jul. 8, 1997

[54] HYDROPHOBIC POLYMERS FROM WATER-SOLUBLE MONOMERS AND THEIR USE AS CHROMATOGRAPHY MEDIA

[75] Inventors: Stellan Hjertén; Jia-Li Liao, both of Uppsala, Sweden

[73] Assignee: Bio-Rad Laboratories, Inc., Hercules, Calif.

[21] Appl. No.: 400,419

[22] Filed: Mar. 2, 1995

Related U.S. Application Data

[63] Continuation of Ser. No. 123,366, Sep. 17, 1993, abandoned, which is a continuation-in-part of Ser. No. 860,613, Mar. 30, 1992, abandoned, which is a continuation of Ser. No. 518,347, May 3, 1992, which is a continuation-in-part of Ser. No. 297,501, Jan. 13, 1989, abandoned.

[51] Int. Cl.$^6$ .................................................. B01D 15/08
[52] U.S. Cl. .................................. 210/198.2; 210/502.1; 210/635; 210/656; 95/88; 96/101
[58] Field of Search ............................ 210/198.2, 502.1, 210/635, 656, 659, 198.3; 422/70; 96/101; 95/88; 436/161

[56] References Cited

U.S. PATENT DOCUMENTS

| | | | |
|---|---|---|---|
| 3,298,925 | 1/1967 | Mosbach | 195/66 |
| 3,867,329 | 2/1975 | Halpern | 210/360.1 |
| 3,878,092 | 4/1975 | Fuller | 210/198.2 |
| 4,090,919 | 5/1978 | Chibata | 210/691 |
| 4,127,468 | 11/1978 | Alfenaar | 204/123 |
| 4,174,414 | 1/1979 | Sasaki | 156/254 |
| 4,201,766 | 5/1980 | Grollier | 424/70 |
| 4,340,483 | 7/1982 | Lucas | 210/198.2 |
| 4,352,884 | 10/1982 | Nakashima | 435/180 |
| 4,415,631 | 11/1983 | Schutijser | 210/198.2 |
| 4,474,663 | 10/1984 | Nakajima | 210/635 |
| 4,483,773 | 11/1984 | Yang | 55/386 |
| 4,565,832 | 1/1986 | Kobashi | 502/402 |
| 4,675,113 | 6/1987 | Graves | 210/198.2 |
| 4,743,373 | 5/1988 | Rai | 210/198.2 |
| 4,747,956 | 5/1988 | Kiniwa | 210/690 |
| 4,793,920 | 12/1988 | Cortes | 210/198.2 |
| 4,808,125 | 2/1989 | Good | 210/198.2 |
| 4,927,531 | 5/1990 | Sakamoto | 210/198.2 |
| 5,017,610 | 5/1991 | Hagen | 210/198.2 |
| 5,114,577 | 5/1992 | Kusano | 210/198.2 |
| 5,135,650 | 8/1992 | Hjerten | 210/198.2 |
| 5,159,049 | 10/1992 | Allen | 524/56 |
| 5,202,007 | 4/1993 | Kozulic | 204/182.8 |
| 5,306,404 | 4/1994 | Notsu | 204/182.8 |
| 5,334,310 | 8/1994 | Frechet | 210/198.2 |

FOREIGN PATENT DOCUMENTS

| | | | |
|---|---|---|---|
| 1442443 | 12/1969 | Germany | 210/198.2 |
| 6803739 | 6/1969 | Netherlands | 210/198.2 |
| WO90/07965 | 7/1990 | WIPO | 210/198.2 |

OTHER PUBLICATIONS

Patent and Trademark Office Translation PTO 91–4925 of Netherlands Patent Application 6803739, Oct. 1991, pp. 1–15.

Mikes Laboratory Handbook of Chromatographic and Allied Methods, John Wiley, New York, 1979, pp. 335, 336, 343–347, & 412–414.

*Primary Examiner*—Ernest G. Therkorn
*Attorney, Agent, or Firm*—Townsend and Townsend and Crew LLP

[57] ABSTRACT

Macromolecular species in a liquid sample are chromatographically separated in a separation medium formed by polymerization of monomers in an aqueous solution with a sufficient amount of crosslinking agent to cause aggregation and precipitation of the polymer chains. The medium is either formed in the column in which chromatography is to take place as a continuous although channeled bed, or in a separate reaction vessel and then transferred to the column in comminuted form as a packed bed. Improvements in the performance of the bed are achieved by compression of the bed.

18 Claims, 25 Drawing Sheets

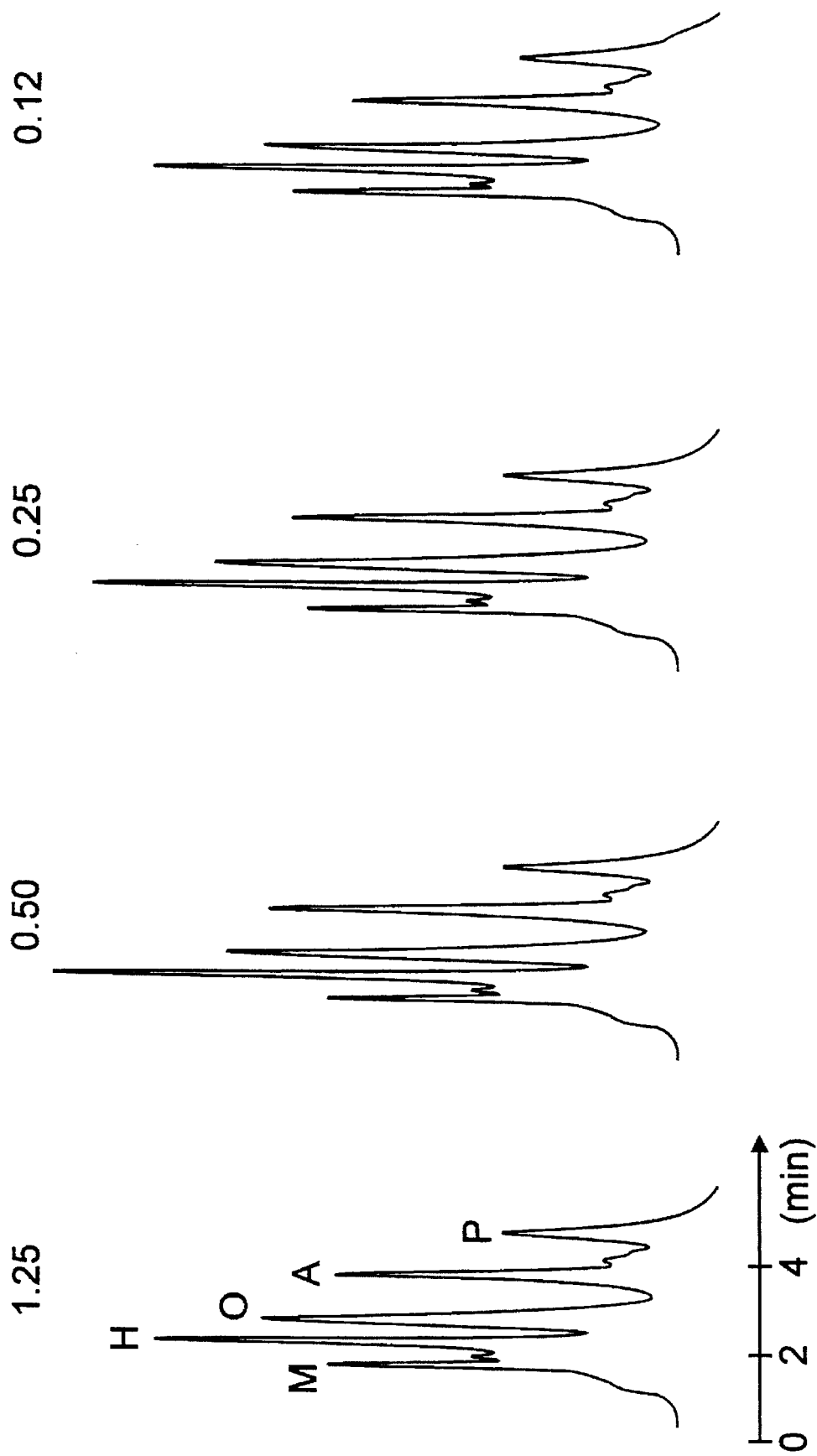

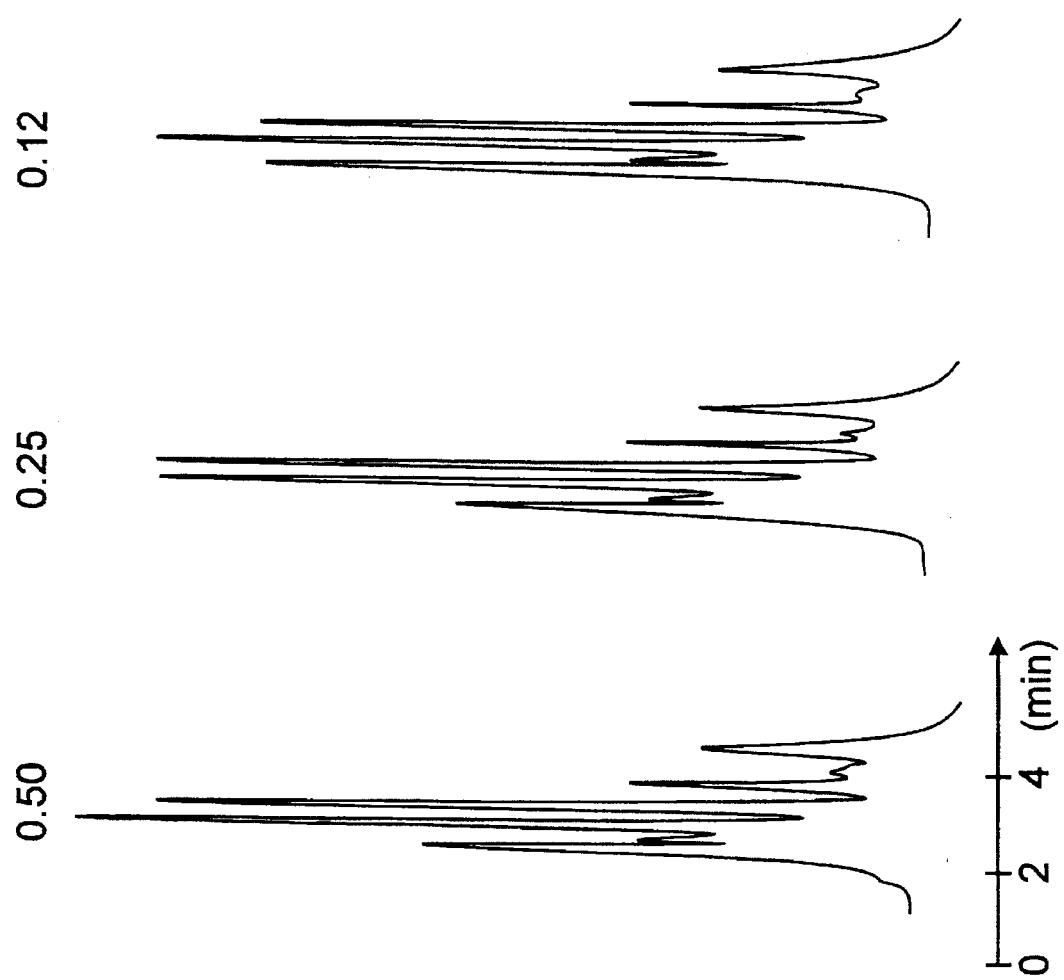

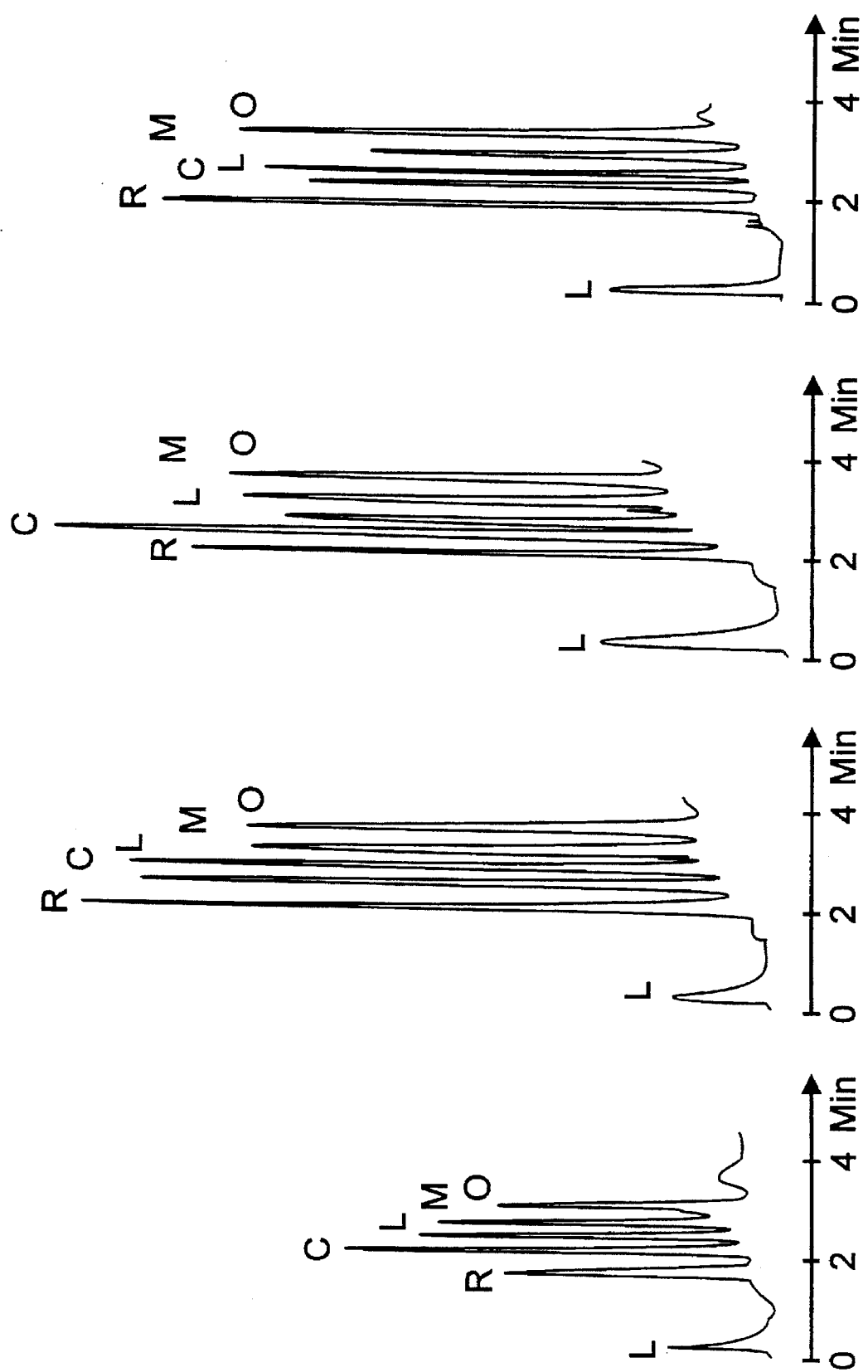

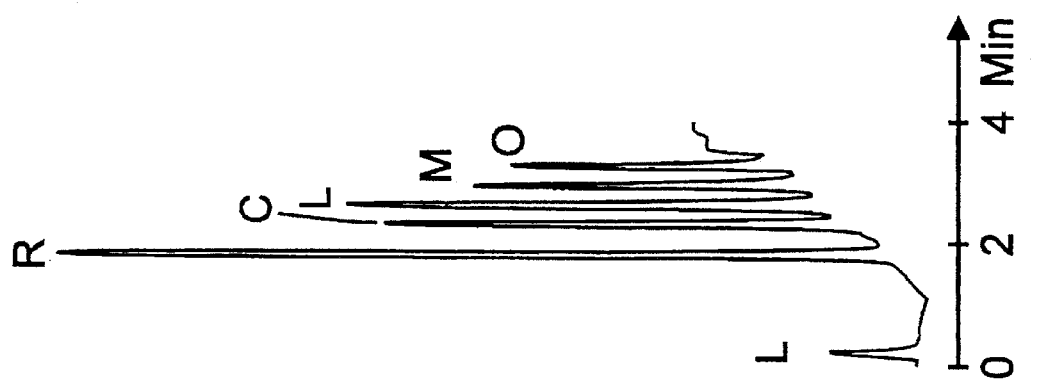
Fig. 7l
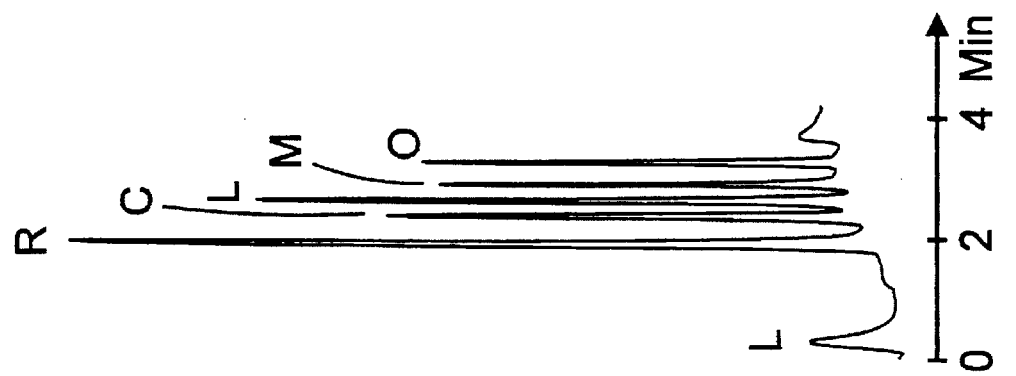
Fig. 7k
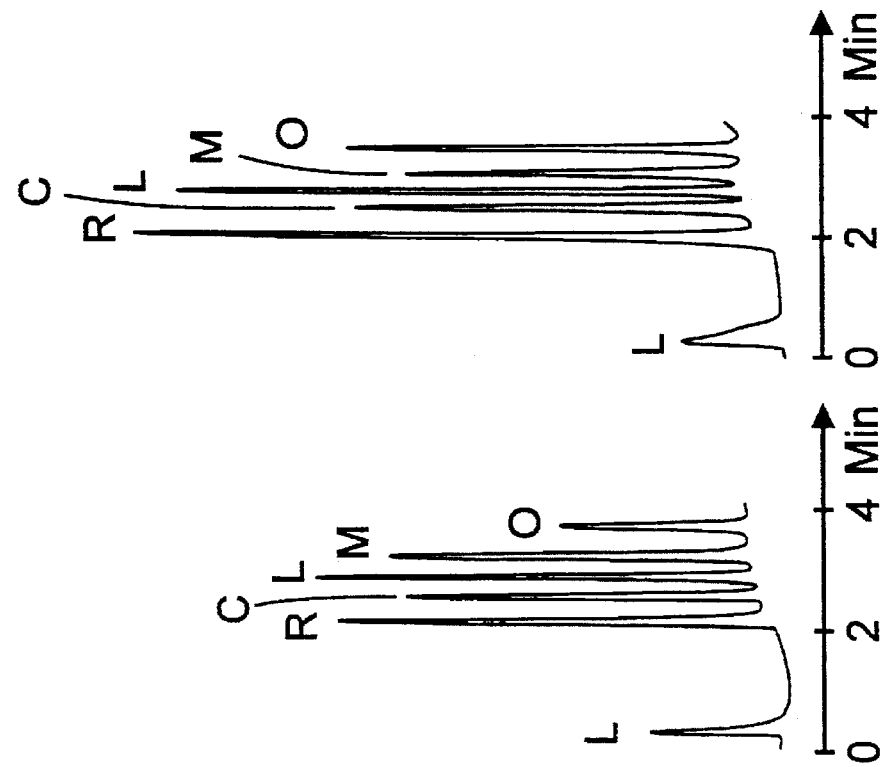
Fig. 7j
Fig. 7i

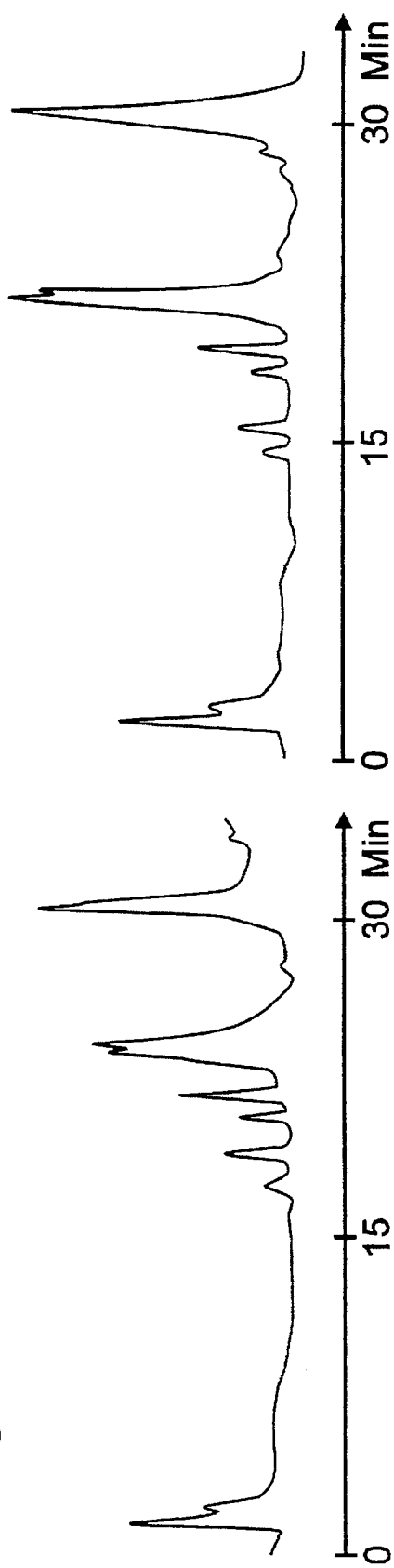
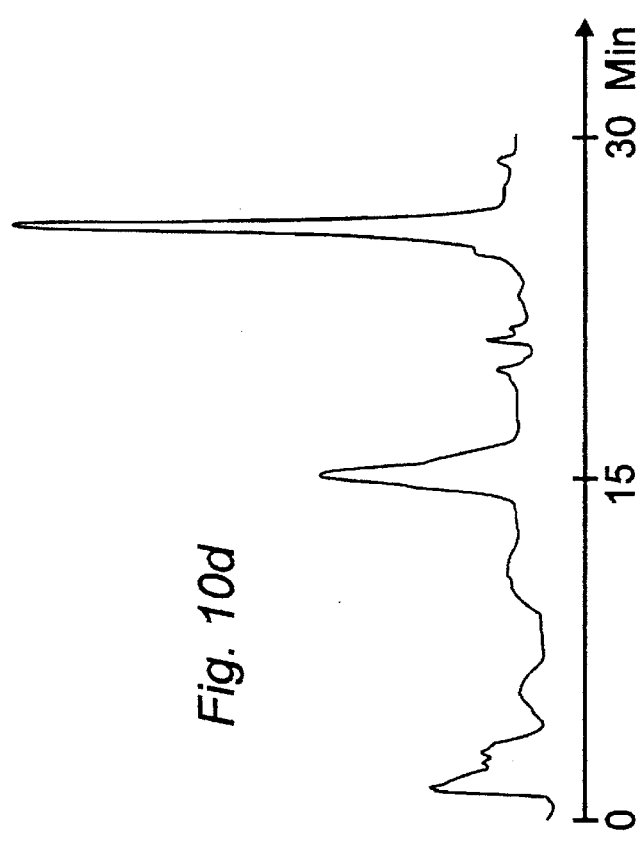
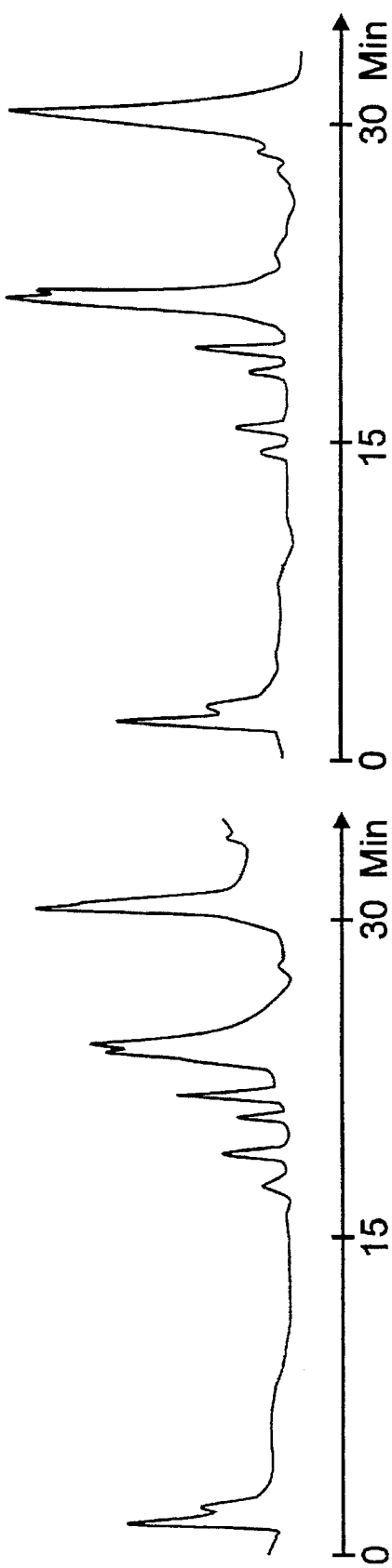
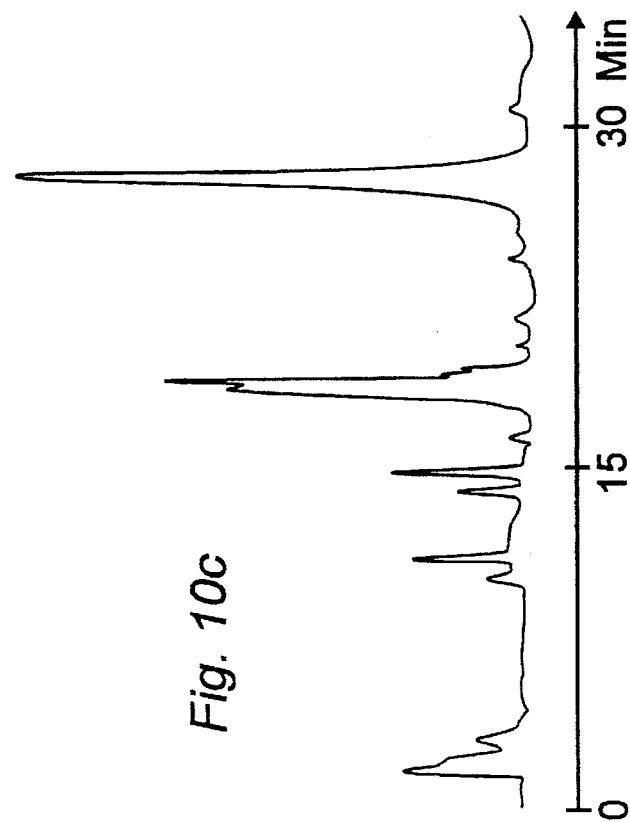
Fig. 10a
Fig. 10b
Fig. 10c
Fig. 10d

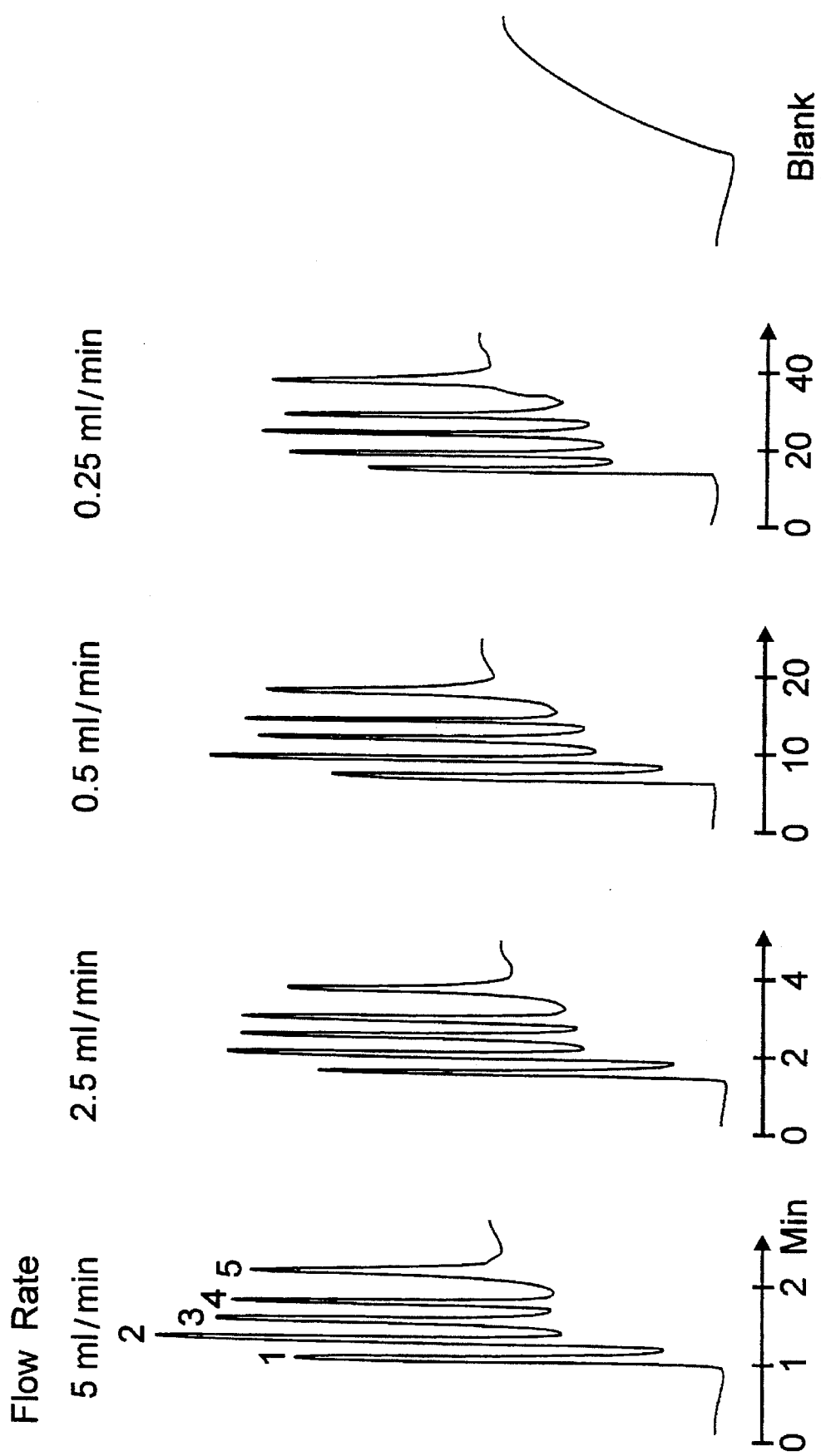

HYDROPHOBIC POLYMERS FROM WATER-SOLUBLE MONOMERS AND THEIR USE AS CHROMATOGRAPHY MEDIA

CROSS REFERENCE TO RELATED APPLICATIONS

This application is a continuation of application Ser. No. 08/123,366, filed Sep. 17, 1993, now abandoned, which, in turn, is a continuation-in-part of application Ser. No. 07/860,613, filed Mar. 30, 1992, now abandoned, which is a continuation of application Ser. No. 07/518,347, filed May 3, 1990, now abandoned, which was a continuation-in-part of application Ser. No. 07/297,501, filed Jan. 13, 1989, now abandoned.

This invention relates to chromatographic separations based on common chromatographic properties such as molecular size, charge, hydrophobicity, and bioaffinity, and also to chromatographic separation media useful for such separations.

BACKGROUND OF THE INVENTION

Conventional high performance liquid chromatography (HPLC) involves the passage of a sample through a bed of beads. It is not possible, however, to achieve a perfectly packed bed. Heterogeneities in packed beds give rise to zone broadening, which is detrimental to resolution and solute detection and identification. Further disadvantages of packed beds are the time-consuming and expensive steps involved in preparing the beads, sieving the beads to isolate those of the desired size, and packing the column with the beads.

SUMMARY OF THE INVENTION

It has now been discovered that these disadvantages and others can be avoided by the use of a chromatographic separation medium formed by polymerization of two or more water-soluble monomers in an aqueous medium, wherein at least one of the monomers is a crosslinking agent present in high proportion, the medium optionally containing dissolved salts or hydrophilic polymers to reduce the solubility of the polymer resulting from the polymerization of the monomers. The monomers are generally polar compounds which contain a carbon-carbon double bond (C=C), and have both hydrophobic and hydrophilic character. Upon polymerization and crosslinking, the carbon-carbon double bonds are converted to the more hydrophobic carbon-carbon single bonds (C—C). This results in an increase in hydrophobicity, and the resulting polymer is so hydrophobic that it aggregates (and thereby precipitates) by hydrophobic interactions. Since the polymers contain many hydrophobic sites, the polymer chains are bonded to each other through multiple points of attachment, resulting in a particularly strong bonding. The high degree of crosslinking produces an extensive hydrophobic branched-chain network of carbon-carbon single bonds which shields the hydrophilic regions and thereby further shifts the hydrophobic-hydrophilic balance toward the hydrophobic. This further promotes and facilitates the aggregation and precipitation of the polymeric material in the aqueous medium. Scanning electron microscopy shows that the bed consists of aggregated particles with a diameter of around 0.5 µm.

In preferred embodiments of the invention, the aggregation of the hydrophobic polymer chains is further strengthened (and the rate of precipitation increased) by performing the polymerization in the presence of a hydrophilic polymer or an inorganic salt with sufficient hydrophilic character to reduce the solubility of the hydrophobic polymer.

The medium is particularly well adapted for use in tubular chromatographic columns such as those used in HPLC and in capillary chromatography. The medium may either be formed directly in the column in which it will be used, or it may be formed in a separate reaction vessel, then comminuted to particulate form and transferred to the column. When formed in the column itself, the medium will exist in the form of a continuous, coherent gel plug filling the column interior and spanning its width, and permeated by channels large enough to permit the passage of a solute. When first formed outside the column and then comminuted and transferred to the column, the medium will exist in the form of a packed bed of clusters of gel particles. Regardless of which method is used, the walls of the channels or the surfaces of the particles provide the contact surfaces for chromatographic separations. These surfaces can be used without further chemical treatment, or they can be coated, derivatized or both to modify or enhance the surface interaction properties of the medium, rendering it suitable for any of the wide variety of separation technologies, such as molecular sieve, ion exchange (either cation or anion), hydrophobic interaction, affinity, boronate, and dye ligand chromatography.

It has also been discovered that separation media in accordance with this invention can be compressed to form a more dense bed which offers improved chromatographic performance. These and other features and advantages are described in detail below.

BRIEF DESCRIPTION OF THE DRAWINGS

FIGS. 3a through 3g are a series of chromatograms taken in anion exchange chromatography experiments on a column prepared in accordance with the invention.

FIGS. 7a through 7l are a series of chromatograms representing reversed-phase chromatography of a standard protein mixture using a variety of beds in accordance with the present invention, showing the effects of variations in several bed parameters on the performance of the bed.

FIGS. 10a through 10d are a series of chromatograms representing reversed-phase chromatography of BrCN-cleaved cellulase using the bed of FIG. 7k, showing the effect of varying the temperature.

FIGS. 17a through 17d are chromatograms of a standard protein mixture on a cation exchange column prepared in accordance with the invention, taken at different flow rates to compare peak resolution. FIG. 17e is a blank to show the baseline.

DETAILED DESCRIPTION OF THE INVENTION AND PREFERRED EMBODIMENTS

Figure 1:
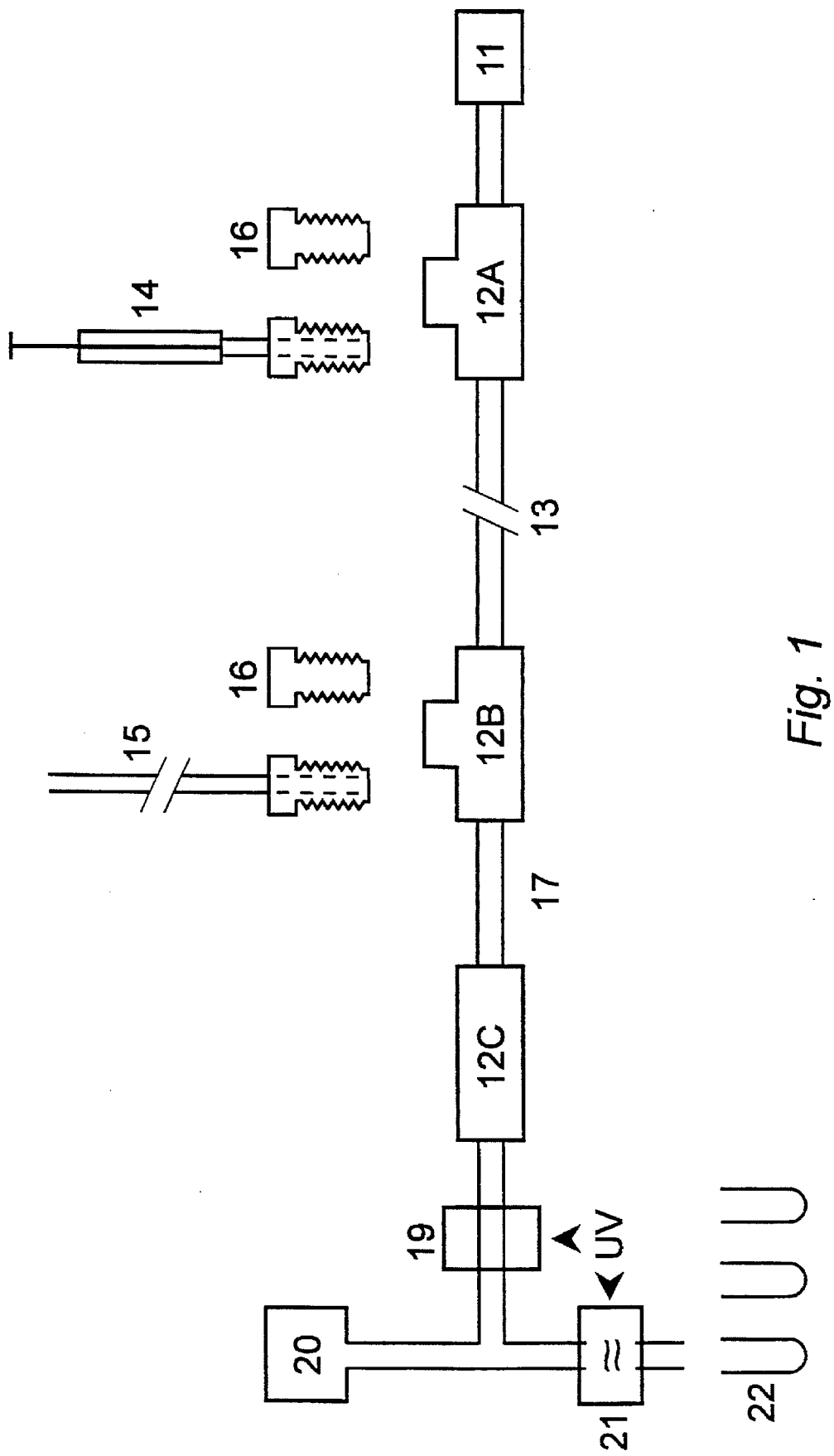
FIG. 1 is a block diagram of a microcolumn chromatography system for use in the practice of the present invention.

Examples of monofunctional monomers (hereinafter referred to as "monomers") and polyfunctional monomers (hereinafter referred to as "crosslinking agents") bearing the qualities described above and suitable for use in the present invention are generally those which are sufficiently hydrophilic to form aqueous solutions. The monomers and crosslinking agents may be charged or uncharged. The solubility of these species in water is preferably at least about 10%. Examples are vinyl, acrylic and methacrylic monomers. Preferred examples are vinyl acetate, vinyl propylamine, acrylic acid, butyl acrylate, acrylamide, methacrylamide, glycidyl methacrylate, glycidyl acrylate and methylene-bis-acrylamide.

When it is desired to derivatize the polymers by the attachment of functional groups, the monomers from which the polymers are formed may also contain reactive groups such as epoxide groups or hydroxyl groups to which covalent attachment is readily achieved. Monomers containing such groups are thus also within the scope of this invention. The monomers may be used singly or in combinations to vary the properties or qualities of the resulting polymer, including controlling the distibution and density of any functional groups present.

Crosslinking agents suitable for use in the present invention include any such bifunctional species capable of reacting with the monomer in a crosslinking manner. For polyacrylamides and polymers of other forms of acrylic acid, examples of suitable crosslinking agents are bisacrylamides, diacrylates, and a wide range of terminal dienes. Specific examples are dihydroxyethylenebisacrylamide, diallyltartardiamide, triallyl citric triamide, ethylene diacrylate, bisacrylylcystamine, N,N'-methylenebisacrylamide and piperazine diacrylamide.

The quantities of monomer and crosslinking agent are conveniently characterized by two parameters, one representing the combined concentrations of monomer and crosslinking agent in the polymer-forming solution, and the other representing the proportion of crosslinking agent relative to the total of monomer and crosslinking agent. The first is conveniently expressed as a weight/volume percent, defined as milligrams of monomer plus crosslinking agent per milliliters of solution, multiplied by 0.1, and is represented herein by the symbol "T". The second is conveniently expressed as a weight/weight percent, defined as milligrams of crosslinking agent divided by milligrams of crosslinking agent plus monomer, multiplied by 100, and is represented herein by the symbol "C". For monomers and crosslinking agents expressed generically, the weight/volume percent "C" is replaced by the mole fraction of crosslinking agent relative to the total of monomer plus crosslinking agent.

For best results in accordance with the present invention, the value of T ranges from about 2% to about 30%, and preferably from about 5% to about 15%. Likewise, the mole fraction of crosslinking agent relative to the total of monomer plus crosslinking agent ranges from about 0.10 to about 0.70, preferably from about 0.15 to about 0.55, and most preferably from about 0.25 to about 0.45.

The inorganic salt referred to in the "Summary of the Invention" is included in the polymer-forming solution to increase the hydrophobic interaction between the hydrophobic groups on the polymer, and thereby enhance the precipitation of the polymer. This effect is known in the art as the "salting out" effect, and a variety of salts are known to exhibit this effect. Prime examples of such salts are sulfate salts, such as ammonium sulfate, sodium sulfate and lithium sulfate. The amount used is not critical and optimal amounts of the salt may vary depending on the salt, the monomer and the cross-linker. For example, relatively small amounts of the salt can be used in systems where the monomer and cross-linker combined have a greater degree of hydrophobicity, while higher amounts will be needed when the monomer and crosslinker have a relatively low degree of hydrophobicity. Enhancement of the hydrophobicity is also achieved by combining a monomer with a second monomer which is more hydrophobic. In most systems, best results will be achieved with an inorganic salt at a concentration of from about 0.15 to about 2.5 equivalents per liter, preferably from about 0.75 to about 1.5 equivalents per liter.

An effect similar to the salting out effect is achieved by the use of hydrophilic polymers. Examples are polyethylene glycol, dextran, methyl cellulose, polyvinyl and non-crosslinked polyacrylamide. The amount of polymer may vary, and the optimum amount in any particular case will depend on the presence and degree of other system parameters which enhance the aggregation. In most cases, the hydrophilic polymer will be effective for this purpose at concentrations within the range of about 5% to about 20%. As an example, a 12% solution of polyethylene glycol will be approximately as effective in this regard as a 60 mg/mL solution of ammonium sulfate.

To form the polymer directly in the column in which it will be used for chromatography, conventional polymerization techniques well known among those skilled in the art may be used. The aqueous solution of monomer and crosslinking agent will generally also contain one or more polymerization catalysts and other conventional additives, and polymerization is permitted to proceed directly in the casing or column tube in which the medium will be used. For microcolumns with inside diameters less than or equal to about 2 mm, it will be advantageous to covalently bind the medium to the inner wall of the column. This may be achieved by binding agents, such as for example vinyl propyl trichlorosilane, according to conventional techniques.

To form the polymer in a separate reaction vessel prior to transferring it to the column, the polymerization is performed in essentially the same manner. Following polymerization the bed is disintegrated into clumps or particles of aggregated polymer chains. This can be done by continuous stirring. Placement of the clumps or particles in the column is then achieved by manually transferring the dispersion to the column. For example, a retaining element such as a grid, porous plug or frit of stainless steel or glass may be placed at one end of the column, and the polymer particle dispersion passed into the column at the other end and through the column so that the particles are retained by the retaining element. The closeness of the packing and hence the density of the bed are controlled by the flow rate of the dispersion into the column.

Regardless of whether the polymer is formed directly in the column as a continuous bed with channels, or formed outside the column, comminuted into particles or clumps and transferred to the column as a packed bed, the performance of the polymer as a chromatographic separation medium is in many cases enhanced by forcible compression of the bed subsequent to its formation and placement in the column. When such compression is to be performed, the bed should not be covalently linked to the wall of the column tube. A possible reason for this improvement is the shortening of the flow path between neighboring polymer particles or channel walls, and hence an increase in the interaction between the solutes and the polymer surface as the sample being separated passes through the bed. Compression may be achieved by the simple application of force, as by a plunger inserted into the column at the end opposite the water-permeable retaining member referred to above, or by the passage of water through the column at a high flow rate, or by any of various other means which will readily occur to those skilled in the art. Compression will usually be done to less than about 75% of the original volume of the polymer, and preferably to about 25% to about 70% of the original polymer volume. In many applications, compression by a factor of at least 5 (i.e., to about one-fifth of the noncompressed volume), and even by a factor of about 10 to about 15, is desirable.

The channel walls of the polymer may be chemically modified to provide it with a selected chromatographic character as appropriate for particular types of separations. Functional groups may be copolymerized into the structure initially, or the surface of the polymer, once formed, may be chemically modified. For example, non-polar ligands may be covalently attached to the polymer to improve its effectiveness as a medium for reversed-phase chromatography. Examples of nonpolar ligands are long-chain saturated aliphatic groups such as linear chains of 6 or more carbon atoms. Ligands of 8 to 18 carbon atoms are particularly useful in this regard. Covalent attachment may be achieved through conventional linkages at the polymer surface, using functional groups on monomers forming the polymer backbone or on secondary monomers incorporated into the backbone as described above. The polymer may likewise be rendered suitable for cation or anion exchange chromatography by the covalent attachment of appropriately charged functional groups to the polymer backbone, or by the conversion of groups already on the backbone to charged moieties. A still further treatment of the polymer is the coating of the polymer with hydrophilic species by covalent attachment, to reduce non-specific interaction. The coated polymer may then be derivatized as desired to achieve a specific type of interaction. When used in a chromatographic separation, the resulting polymer offers greater resolution. Coating of the polymer with hydrophilic species may further be used as a means of providing more coupling sites for derivatization, by selecting a coating with a high density of functional groups available for coupling.

Once prepared by any of the techniques described above, the separation medium of the present invention may be used for a wide variety of separations, including peptides, proteins, and other types of mixtures in biological or other samples. The mobile phase is an aqueous phase, preferably a buffer solution with a pH of about 1.0 to about 13.0, preferably within the range of about 7.0 to about 8.5, and flow is achieved either by pumping or by gravity flow. Detection of the eluting solutes is readily achieved by conventional means, either in the column itself, using staining methods if necessary, or outside the column at the downstream end. Separation media of this type are particularly effective for the separation of species having molecular weights ranging from about 1,000 to about 1,000,000.

The following examples are offered strictly for purposes of illustration, and are intended neither to limit nor to define the invention in any manner.

MATERIALS

Electrophoresis purity reagents acrylamide, methacrylamide, N,N'-methylene-bisacrylamide (BIS), piperazine diacrylamide, tris(hydroxymethyl)aminomethane hydrochloride (Tris-HCl), N,N, N', N'-tetramethylethylenediamine (TEMED), ammonium persulfate (HPLC grade), octadecanol, boron trifluoride etherate, allyl glycidyl ether, trifluoroacetic acid (TFA), sodium borohydride, 1,2-epoxyoctane, 1,2-epoxyoctadecane, N-allyldimethylamine, butyl acrylate, acrylic acid, acetonitrile, and 1,3-di-trimethylol propane (DTMP) were obtained from Bio-Rad Laboratories, Inc. (Hercules, Calif., U.S.A.), Fluka AG (Buchs, Switzerland), E. Merck (Darmstadt, Federal Republic of Germany), Viking Chemical Company (Minneapolis, Minn., U.S.A.), Aldrich (Steinhelm, West Germany). Dextran T-10 (molecular weight 10,000) was obtained from Pharmacia LKB Biotechnology AG (Uppsala, Sweden); ethyl cellulose (T-50, 48 centipoise) was obtained from Hercules Powder Company (Wilmington, Del., U.S.A.). A subfraction of *Trichoderma reesei* cellulases was a gift from Dr. Göran Pettersson of the University of Uppsala, Department of Biochemistry, Biomedical Center, Uppsala, Sweden. All other proteins were obtained from Sigma Chemical Company (St. Louis, Mo., U.S.A.)

APPARATUS

An HPLC pump (Model 2150), pump controller (Model 2152), recording integrator (Model 2220) and recorder (Model 2210) were used in these experiments, and were obtained from Pharmacia LKB Biotechnology AB (Bromma, Sweden); a UV monitor (Model 1306) from Bio-Rad Laboratories, Inc., was used. A syringe pump for off-tube detection of proteins separated on the microbore HIC (hydrophobic interaction chromatography) column (i.d.=0.3 mm), constructed at the University of Uppsala, was used. Stainless steel tees were obtained from Upchurch Scientific, Inc. (Oak Harbor, Wash., U.S.A.). Teflon tubing (i.d.=0.3 mm) was obtained from Skandinaviska GeneTec AB (Kungsbacka, Sweden). Other equipment used included a Model 5000 liquid Chromatograph from Varian (Palo Alto, Calif., U.S.A.) and a loop injector from Rheodyne (Berkeley, Calif., U.S.A.).

Column tubes of stainless steel, silica and Plexiglas were used. These tubes were equipped as needed with a metal or glass frit at one end and a movable plunger at the other.

EXAMPLE 1

A glass wool plug was placed in a Pasteur pipette at the top of the constricted region of the pipette. A length of plastic tubing fitted with a hose clamp was secured to the pipette tip.

A buffer solution containing 0.01M Tris-HCl and 10% (weight/volume) sucrose at pH 7.5 was poured into the pipette. The hose clamp was then opened. When the buffer level reached the glass wool, the hose clamp was closed to stop the buffer flow.

A deaerated mixture was then poured into the pipette and allowed to polymerize. The mixture consisted of 1 mL of an aqueous solution of acrylamide and N,N'-methylenebisacrylamide (at concentrations and proportions listed below), 6 µL of a 10% (weight/volume) solution of ammonium persulfate, and 1 µL of TEMED.

Once the solution polymerized, it formed a non-water-soluble continuous structure spanning the width of the pipette above the glass wool. A sample consisting of the following components was then applied to the top of the polymer structure:

TABLE 1

| | |
|---|---|
| phycoerythrin | M.W. 290,000 |
| phycocyanin | M.W. 135,000 |
| cytochrome | M.W. 13,000 |
| bromophenol blue | M.W. 1,000 |

A buffer solution consisting of 0.01 M Tris-HCl, pH 7.5, was layered above the sample, and the sample and buffer solution were permitted to flow through the pipette by gravity flow. A variety of polyacrylamide compositions and buffer solution flow rates were used, as listed in the table below. In this table, the symbol T designates the concentration in weight/volume percent of the acrylamide and N,N'-methylenebisacrylamide combined in the forming solution, the symbol C designates the proportion of N,N'-methylenebisacrylamide relative to the combination of acrylamide and N,N'-methylenebisacrylamide expressed in weight/weight percent, and the last column represents the flow rates in values relative to each other for each C value. Note that C=10 corresponds to a mole fraction of 0.05 and C=60 corresponds to a mole fraction of 0.69. The flow rate given for T=4, C=60 is equivalent to about 4–5 hours for the entire elution. Direct comparisons can be made among flow rates for the various C values with a single T value.

TABLE 2

| Polymer Composition | | Gravity |
|---|---|---|
| T (%) | C (%) | Flow |
| 4 | 60 | 0.8 |
| 4 | 50 | 0.3 |
| 4 | 40 | <0.3 |
| 4 | 30 | <0.3 |
| 4 | 20 | 0 |
| 3 | 60 | 2.5 |
| 3 | 50 | 1.8 |
| 3 | 40 | <1.8 |
| 3 | 20 | 0 |
| 2 | 60 | 3 |
| 2 | 50 | 5 |
| 2 | 30 | 0 |
| 20 | 30 | 0 |
| 20 | 15 | 0 |
| 10 | 30 | 0 |
| 6 | 10 | 0 |
| 6 | 20 | 0 |
| 6 | 30 | 0 |

In those runs where a positive gravity flow was detectable, the four components listed above separated into discrete bands, in order of increasing molecular weight, with the component of highest molecular weight (phycoerythrin) showing the greatest mobility through the column.

EXAMPLE 2

A. Preparation of a Continuous Bed for Anion Exchange Chromatography

BIS (0.24 g) and N-allyldimethylamine (0.12 mL) were dissolved, with stirring, in 9.5 mL of 0.01M sodium phosphate, pH 6.4. The pH was adjusted to 7 with 2N HCl (approximately 400µL). Ammonium sulfate (0.5 g) and 100 µL of a 10% (weight/volume) aqueous solution of ammonium persulfate were added. Following deaeration and addition of 100 µL of a 5% (volume/volume) solution of TEMED, the reaction mixture was poured into a 6 mm (i.d.)×350 mm column tube. The final concentration of BIS was thus about 2.4% (weight/volume).

Polymerization was allowed to proceed for 5 hours, after which time 0.01M Tris-HCl (pH 8.5) was pumped into the column tube at a flow rate of 0.5 mL/min. This caused the height of the polymer plug to decrease continuously. The pumping was continued until the height of the polymer plug became constant at about 60 mm. The polymer plug was then compressed further manually with the aid of the upper piston, to a final height of about 35 mm. The piston was then fixed in this position to prevent the polymer plug from expanding upon elution at lower flow rates. The compression thus decreased the height of the polymer plug to about one-tenth of its uncompressed height.

B. Preparation of a Continuous Bed for Hydrophobic Interaction Chromatography With stirring, 0.48 g of BIS was dissolved in 20 mL of water. Following addition of 0.08 mL of butylacrylate, 0.3 g of ammonium sulfate, and 200 µL of a 10% (weight/volume) solution of ammonium persulfate, the mixture was deaerated and supplemented with 200 µL of a 5% (volume/volume) solution of TEMED. Both the 6-mm column tube (length: 450 mm) and the 0.3-mm tube (length: 600 mm) were filled with this catalyzed monomer solution, which was allowed to polymerize for 5 hours.

The 6-mm diameter bed was compressed to a height of 38 mm by pumping with a 0.01M sodium phosphate solution (pH 7.0) containing 2.5M ammonium sulfate, followed by manual pressing down of the piston as described above in section A of this example.

The item numbers in this and the following section refer to FIG. 1, which shows the HPLC pump 11, zero dead volume stainless steel tees 12a, b, unions 12c, gradient teflon tubing 13, syringe 14, fused silica tubing for the introduction of the buffer gradient and sample 15, boreless stainless steel nut 16, microcolumn of fused silica tubing 17, post-column nut of fused silica tubing for on-line detection 18, on-tube detector 19, syringe pump 20, off-tube detector 21 and fraction collector 22.

To prepare the microbore bed, a union 12c containing a metal frit (pore diameter 2 μm) was attached to the microcolumn tube 15 (i.d. 0.3 mm). The polymer plug was compressed at a flow rate of 0.01 mL/min from a height of 600 mm to 120 mm, and then further to 70 mm by increasing the pressure to 100 bar for 5 minutes. The upper segment of the column tubing above the polymer bed was cut off and coupled to the teflon tubing via the tee 12b.

C. Formation of Small-Volume Salt Gradients for Elution of the Microcolumn

A 8.5-mL linear salt gradient was generated in a 10-mL cylinder (i.d.=13 mm) with the aid of the HPLC equipment. The gradient was formed from 2.25M ammonium sulfate (at the bottom) to 0.25M ammonium sulfate (at the top) in 0.01M sodium phosphate buffer (pH 7.0). Using a colored pen, the cylinder was graduated from the bottom into 17 equal sections, with the distance between each pair of adjacent divisions corresponding to 0.5 mL. After equilibration of the column with 0.01M sodium phosphate buffer (pH 7.0) containing 2.25M ammonium sulfate, the stainless steel nuts 16 were replaced with a 50-μL syringe 14 and a length of 0.6-μL tubing 15. The gradient tubing 13 and the 0.6-μL tubing 15 were then filled with 0.01M sodium phosphate (pH 7.0) containing 2.25M ammonium sulfate using the HPLC pump 11. The tubing 15 was immersed in the gradient salt solution, and 2 μL of the solution at the center of each section was drawn into the tubing with the 50-μL syringe 14, starting with the top section. The final volume of the gradient salt solution was thus 34 μL.

The free end of the filled tubing 15 was dipped into the sample. With the aid of the syringe 14, 1 μL of the sample was drawn into the tubing. The tubing was then immersed into the equilibration buffer and 2 μL of the buffer was drawn into the tubing. By this procedure, the sample was thus introduced into the gradient tubing i3. The syringe 14 and tubing 15 with connecting nuts were then replaced by stainless steel nuts 16 without bores. The pump 11 was then turned on. Since the minimum flow rate of the pump was 0.01 mL/min, the connection between the pump 11 and the tee 12a was loosened until the flow rate in the column was 0.001 mL/min.

Figure 2:
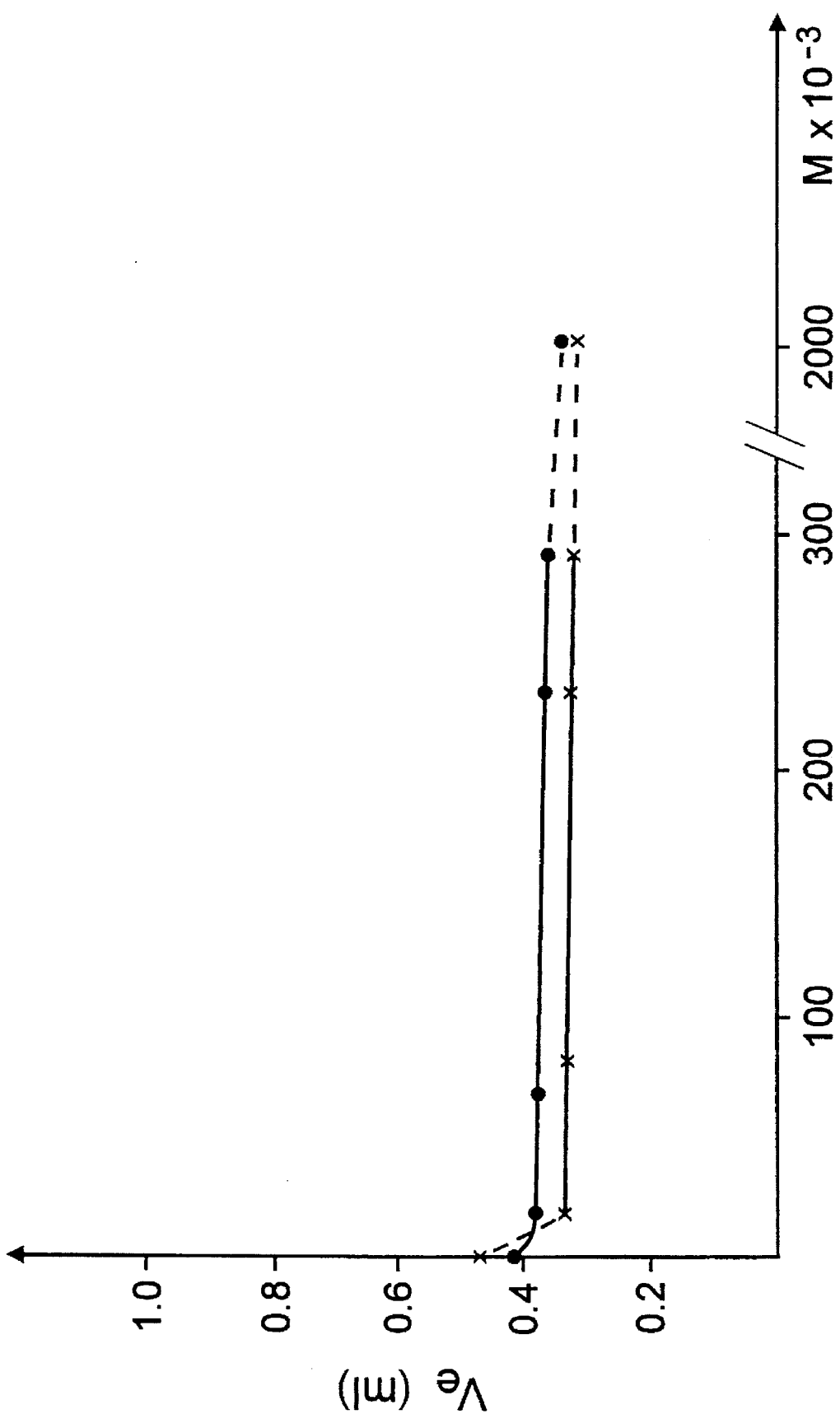
FIG. 2 is a plot of elution volume ($V_e$) vs. molecular weight in a hydrophobic interaction chromatography experiment on a column prepared in accordance with the invention.

C. Determination of Pore Size in the Walls of the Channels in the Polymer Beds The porosity of the beds prepared in both sections A and B above was studied by molecular sieve chromatography, using standard proteins of different molecular weights, plus Dextran 2000 (molecular weight $2\times10^6$) and sucrose. FIG. 2 is a plot of elution volume vs. molecular weight, showing that all components with the exception of sucrose eluted at the same volume. This indicates that neither the proteins nor dextran penetrated into the channel walls. The slight difference in elution volume observed for sucrose indicates that it probably penetrated only a thin surface layer on the channel walls.

D. Scanning Electron Microscopy of the Continuous Polymer Beds

Compressed continuous polymer beds prepared in accordance with sections A and B of this example, together with one prepared for cation exchange chromatography by an analogous procedure, were removed from the column tubes and frozen immediately. Following freeze-drying, aliquots of the beds were examined by scanning electron microscopy, which revealed that each of the beds consisted of aggregated polymer particles (diameter 0.5 μm) with channels of 5 μm width between the aggregates.

E. Determination of the Stability of the Column and the Influence of Flow Rate on Protein Resolution The anion exchange column prepared in section A of this example was equilibrated with 0.01 M Tris-HCl (pH 8.5). A sample was then applied to the bed, the sample consisting of 20 μg each of myoglobin (M), hemoglobin (H), ovalbumin (O), bovine albumin (A), and R-phycoerythrin (P), dissolved in 40 μL of the equilibration buffer. Desorption was then performed at flow rates of 0.12, 0.25, 0.50 and 1.25 mL/min by a 5.0-mL linear salt gradient generated from the equilibration buffer and the same buffer supplemented with 0.43M sodium acetate, pH 8.5. The results are shown in FIGS. 3a (1.25 mL/min), 3b (0.50 mL/min), 3c (0.25 mL/min) and 3d (0.12 mL/min).

The experiment was performed three months later on the same column, following more than fifty runs. The results of these tests are shown in FIGS. 3e (0.50 mL/min), 3f (0.25 mL/min) and 3g (0.12 mL/min). A comparison of the chromatograms in FIGS. 3a–d against those of FIGS. 3e–g shows that the column is both stable and reproducible after repeated use.

Figures 4A, 4B, 4C, 4D, 4E:
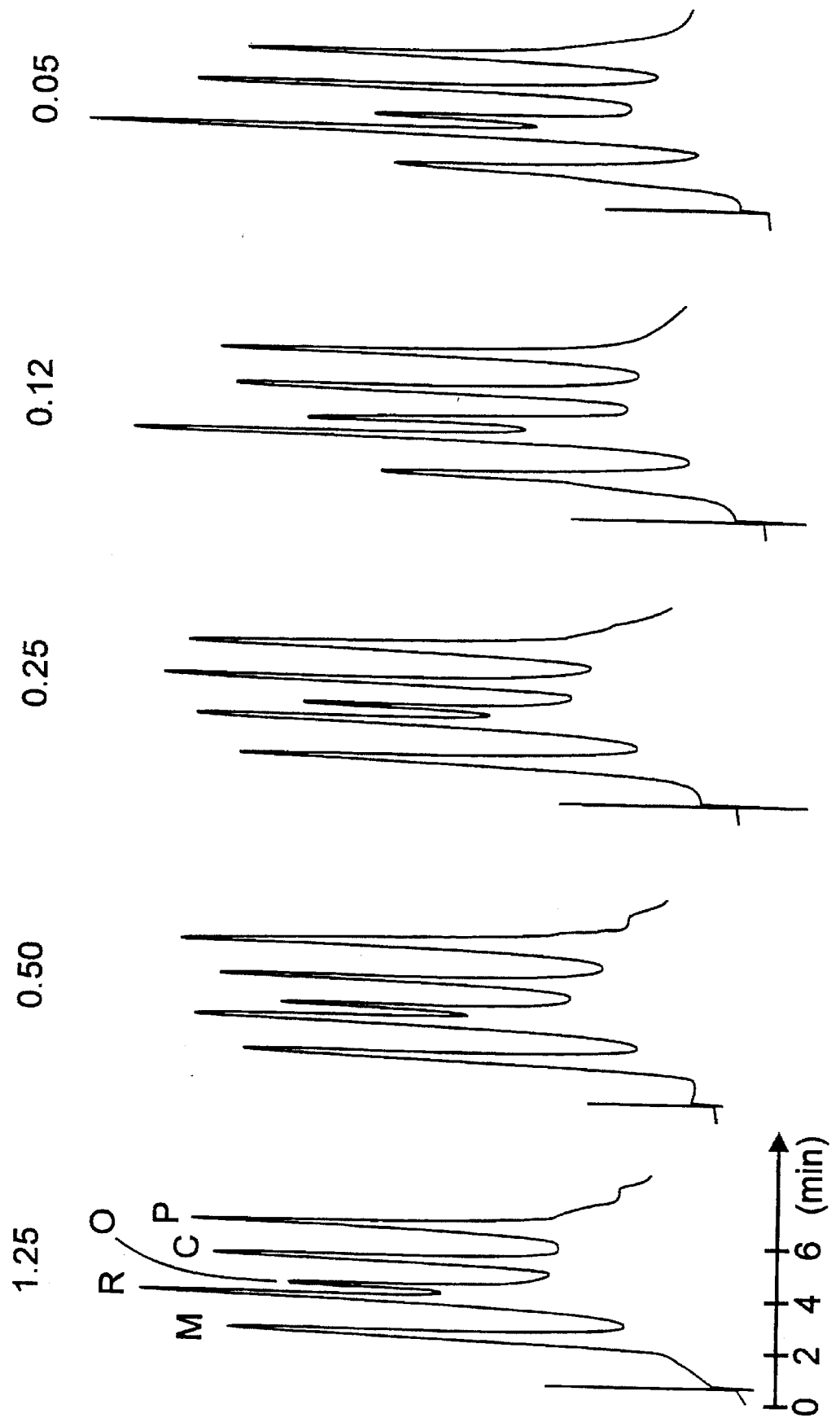
FIGS. 4a through 4d are a series of chromatograms taken in hydrophobic interaction chromatography experiments on a column prepared in accordance with the invention.

A similar experiment was performed on the HIC column of section B of this example. The column was equilibrated with 2.25M ammonium sulfate in 0.01M sodium phosphate, pH 7.0 (the equilibration buffer). The sample consisted of 5–10 μg each of myoglobin (M), ribonuclease (R), ovalbumin (O), α-chymotrypsinogen A (C) and R-phycoerythrin (P) in 25 μL of the equilibration buffer. The separation of these proteins was accomplished with a 7.5-mL negative linear gradient formed from the equilibration buffer, and 0.25M ammonium sulfate in the same buffer, over a range of flow rates. The results are shown in FIGS. 4a (1.25 mL/min), 4b (0.50 mL/min), 4c (0.25 min), 4d (0.12 mL/min) and 4e (0.05 mL/min).

Figure 5A:
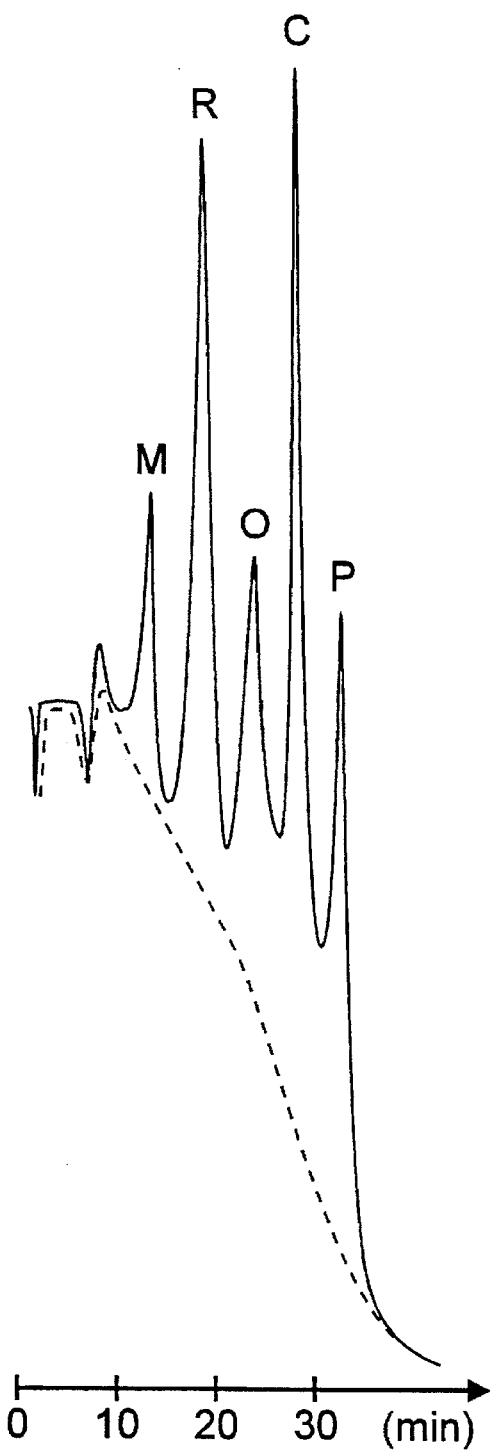
FIGS. 5a and 5b are a pair of chromatograms taken in hydrophobic interaction chromatography experiments on a column prepared in accordance with the invention, showing on-tube and off-tube detection.

F. A Comparison between On-Tube and Off-Tube Detection of Proteins Separated on a Microbore Column The HIC column prepared in section A of this example with dimension 0.3 mm (i.d.)×70 mm was equilibrated with 2.25M ammonium sulfate in 0.01M sodium phosphate, pH 7.0. A sample of volume 1 μL containing 0.4 μg each of myoglobin (M), ribonuclease (R), ovalbumin (O), α-chymotrypsinogen A (C) and R-phycoerythrin (P). A gradient volume of 0.035 mL was used, at a flow rate of 0.001 mL/min. On-tube detection was achieved using a 0.15 mm (i.d.)×30 mm length of fused silica tubing attached to the outlet of the microbore column. The results are shown in FIG. 5a.

Off-tube detection was performed with the use of a flow-through cell with a volume of 8 μL and a light path length of 10 mm, with a Bio-Rad 1306 HPLC UV monitor.

Figure 5B:
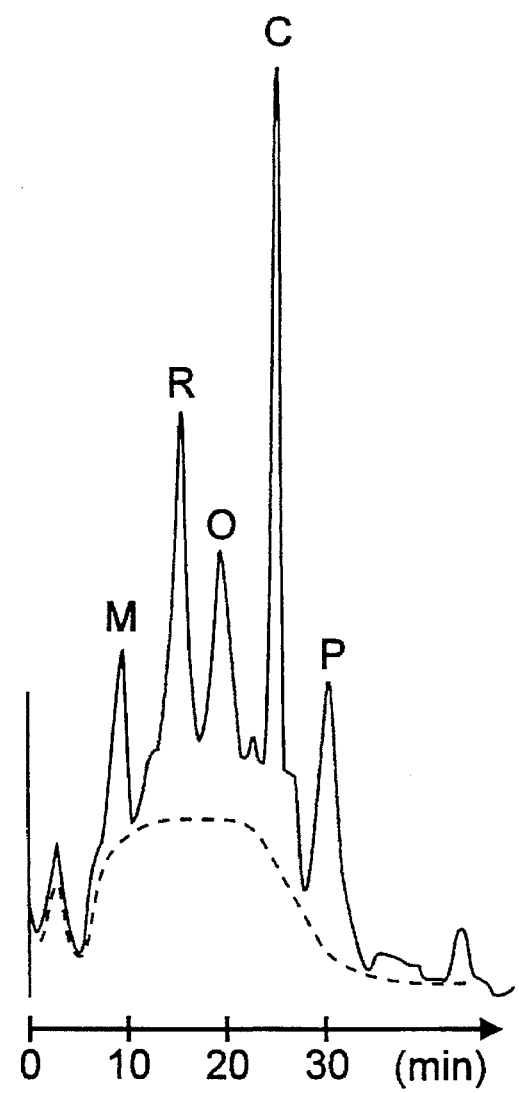

The cross-flow solution, 0.01 M sodium phosphate at pH 7.0, was pumped at the rate of 0.06 mL/min. The results are shown in FIG. 5b.

G. High-Performance Anion Exchange Chromatography of a Cellulase Fraction

Figure 6:
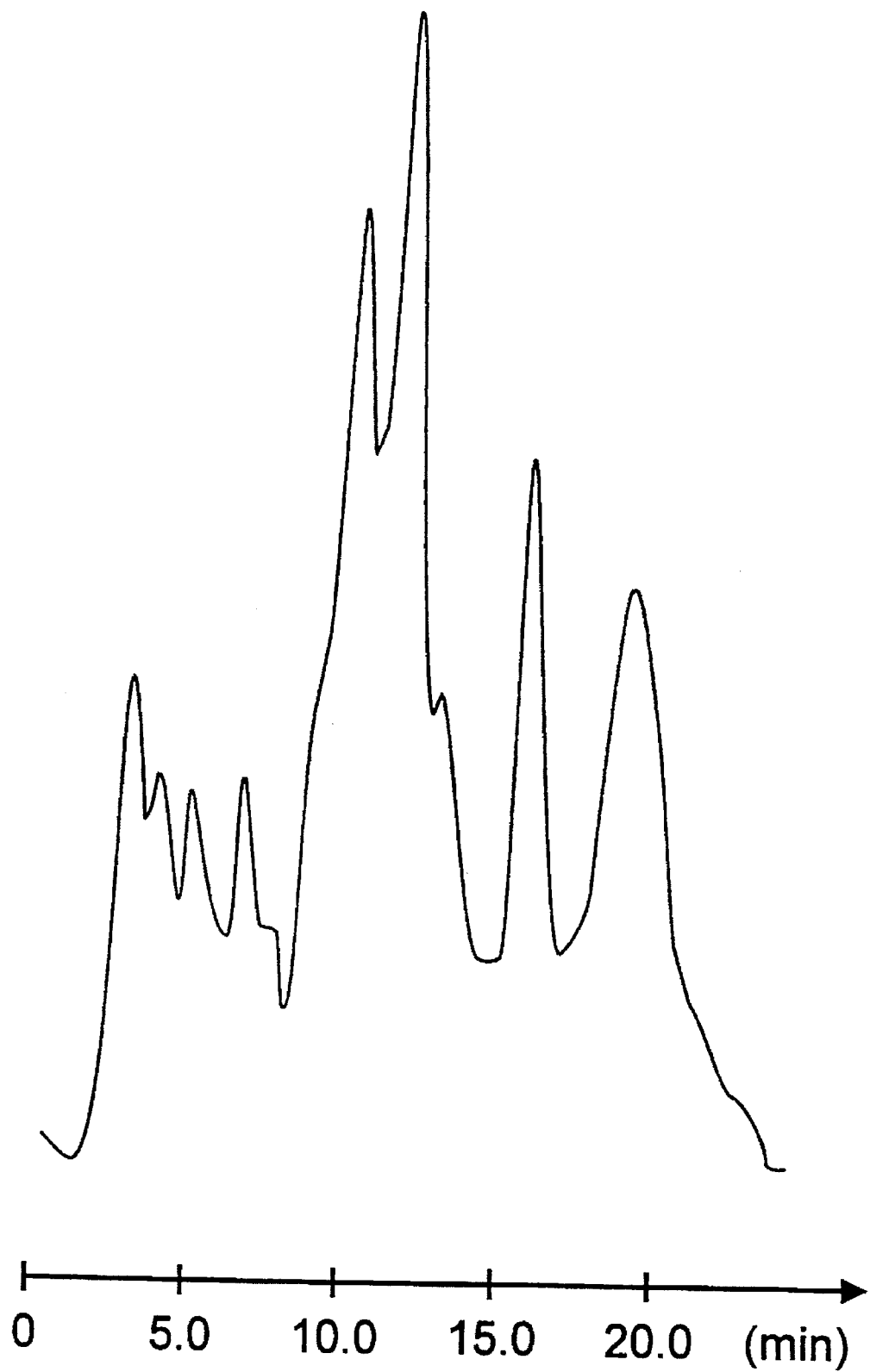
FIG. 6 is a chromatogram of a cellulase fraction taken on an anion exchange column prepared in accordance with the invention.

The anion exchange chromatography column prepared in section A of this example, measuring 6 mm (i.d.)×35 mm, was used to separate a 200 µL sample of a solution containing 250 µg of cellulase. The elution was performed with a 20-mL salt gradient from 0.01M Tris-HCl and the same buffer with 0.25M sodium acetate (pH 8.5) added, at a flow rate of 0.5 mL/min. The results are shown in FIG. 6.

EXAMPLE 3

This example illustrates the preparation of a chromatographic medium in accordance with the present invention, the preparation of derivatized forms of the medium for reversed-phase chromatography, and the use of the derivatized forms in the separation of protein mixtures. The media in this example were epoxy-activated beds synthesized from an aqueous solution and formed as clusters of small particles which were then transfered into the column. The monomers were piperazine diacrylamide, methacrylamide and allyl glycidyl ether. Upon polymerization, these monomers formed epoxy-activated polymers which were then derivatized by covalent attachment of either nonpolar ligands or OH-rich substances. The beds derivatized with nonpolar ligands were used directly for reversed-phase chromatography, while those derivatized with OH-rich substances were first coupled with 1,2-epoxyoctadecane or 1,2-epoxyoctane and then used for reversed-phase chromatography.

The media were prepared as follows. A glass test tube was charged with a 10 mL of an aqueous solution containing methacrylamide and piperazine diacrylamide at a total concentration (T) of 5% (weight/volume)and a crosslinking concentration (C) of 55.9% (weight/volume), plus allyl glycidyl ether at a concentration of 10% (volume/volume) and ammonium sulfate at a concentration of 60 mg/mL. The solution was deaerated in the test tube for 2 minutes, then supplemented with 50 µL of an aqueous solution of 5% (volume/volume) TEMED. Polymerization then proceeded at room temperature.

After 6 hours, the resulting polymer was washed three times with distilled water by centrifugation at 1000 g, and then dehydrated with acetone (four washings). The polymer was then washed with ether and transfered with stirring into 10 mL of ether. With continued stirring, the resulting suspension was added to 35 mL of ether containing 3.14 g of 1-octadecanol, and 0.2 mL of $BF_3$ was added dropwise.

Additional $BF_3$ (0.1 mL) was added after an hour. The continuous stirring resulted in a suspension of polymer particles.

Several preparations were made in this manner, with the reaction time varying among the preparations from 2 to 14 hours. After the designated reaction time for each preparation, each resulting $C_{18}$-derivatized polymer was washed with ether three times to remove unreacted 1-octadecanol, followed by three times with acetone to remove the ether, and finally with distilled water.

The polymers were then placed in stainless steel columns (i.d.=6 mm; height=300 mm) at either a flow rate of 5 mL/min or a flow rate increasing stepwise from 1 mL/min to 5 mL/min, over a thirty-minute period. The polymers were then compressed by a plunger. A standard sample mixture of five proteins—ribonuclease, cytochrome C, lysozyme, myoglobin and ovalbumin—was prepared in distilled water, and each of the columns was loaded with an aliquot of the mixture. HPLC analyses were then performed on a Model 5000 Liquid Chromatograph from Varian (Palo Alto, Calif., U.S.A., using a mobile phase of two solvents in a gradient elution:

Solvent A: 0.1% (volume/volume) TFA in water

Solvent B: 0.1% (volume/volume) TFA in acetonitrile

The gradient progressed from 10% to 70% solvent B in solvent A, with a total volume of 20 mL at a flow rate of 5 mL/min. The eluting solutes were detected by a Model 1306 UV Monitor from Bio-Rad Laboratories, Inc., Hercules, Calif., U.S.A., at 230 nm. The retention times are listed in Table 3.

TABLE 3

Retention Time on Epoxy-Activated Continuous Bed Derivatized With 1-Octadecanol vs. Reaction Time

| Reaction Time (hours) | Retention Time (minutes) | | | | |
|---|---|---|---|---|---|
| | Ribonuclease | Cytochrome C | Lysozyme | Myoglobin | Ovalbumin |
| 2 | 0.4 | 1.6 | 2.2 | 2.6 | 3.0 |
| 3 | 1.7 | 2.2 | 2.5 | 2.8 | 3.2 |
| 4 | 2.2 | 2.7 | 3.0 | 3.3 | 3.8 |
| 6 | 1.8 | 2.3 | 2.6 | 2.9 | 3.2 |
| 8 | 1.7 | 2.4 | 2.7 | 2.9 | 3.4 |
| 14 | 1.9 | 2.2 | 2.6 | 3.0 | 3.5 |

The data in Table 3 indicate that the longest retention times, and consequently the highest ligand density, were achieved with a polymer bed formed by a polymerization reaction which had been permitted to proceed for 4 hours.

The protein capacity of each polymer was then determined, using as a sample a mixture of ovalbumin and myoglobin. The columns used for these tests were prepared as described above and equilibrated with solvent A. The sample injected into each column was 10 µL of a 0.5% (weight/volume) solution of ovalbumin. Once the samples was injected, each column was washed with an amount of solvent A slightly larger than the void volume of the column, at a flow rate of 1 mL/min. The injection and washing steps were then repealed until ovalbumin began to appear in the column effluent. The amount of ovalbumin absorbed by the column was calculated from the number and volume of injections up to that point. The same determination was performed for myoglobin. The results are shown in Table 4. The two figures in each set of parentheses appearing in the row corresponding to a 4-hour reaction time represent values obtained with epoxy-activated beds derivatized with 1,2-epoxyoctadecane and with dextran-coated beds derivatized with 1,2-epoxyoctadecane, respectively (each as opposed to the remaining figurew chih represent epoxy-activated beds derivatized with octadecanol). An increase in capacity indicates an increase in ligand density.

TABLE 4

Protein Capacity of $C_{18}$-Derivatized Bed vs. Reaction Time

| Reaction Time (hours) | Protein Capacity (mg protein/mL compressed bed) | |
| --- | --- | --- |
| | Ovalbumin | Myoglobin |
| 2 | 0.11 | 0.11 |
| 3 | 0.38 | 0.57 |
| 4 | 0.45 | 0.62 |
| | (0.47; 0.81) | (0.81; 1.1) |
| 6 | 0.49 | 0.63 |
| 8 | 0.51 | 0.60 |
| 14 | 0.37 | 0.54 |

The results from Table 4 are consistent with those of Table 3.

To determine the degree to which proteins could be recovered from the $C_{18}$-derivatized polymer prepared with a 4-hour reaction time, the column was loaded with the polymer as described above and equilibrated with solvent A. In separate experiments, 100 μg of protein were injected into the column, and the protein was eluted from the column with solvent B at a flow rate of 1 mL/min. The percent recovery was estimated spectrophotometrically from the volume and absorbance at 280 nm, comparing that of the sample applied against that of the desorbed protein. The results are shown in Table 5.

TABLE 5

Recovery of Proteins from $C_{18}$-Derivatized Bed

| Protein | Recovery (%) |
| --- | --- |
| Ribonuclease | 94 |
| Cytochrome C | 102 |
| Lysozyme | 99 |
| Myoglobin | 98 |
| Ovalbumin | 97 |

For additional experiments, 1,2-epoxyoctadecane was substituted for the 1-octadecanol, and in still others, a total monomer concentration T of 15% (weight/volume) was used rather than 5%. Derivatized versions of the polymers were prepared by reacting the epoxy groups at high pH (0.00032M NaOH, pH 10.5) with —OH groups in glucose, dextran, 1,3-di-trimethylolpropane (DTMP) and polyvinylalcohol (PVA). These groups were attached for the purpose of modifying the walls of the channels in the polymer to render the walls strongly hydrophilic, thereby reducing non-specific interactions. The amounts used were as follows:

glucose: 1.5 g with 20 mL 0.00032M NaOH
dextran: 1 g with 29 mL 0.00032M NaOH plus 50 mg $NaBH_4$
DTMP: 3.7 g with 200 mL 0.00032M NaOH
PVA: 1 g with 60 mL 0.00032M NaOH The reactions were permitted to proceed for eighteen hours, after which time the polymers were washed with distilled water, dehydrated with acetone and suspended in 10 mL of ether. The suspensions were then diluted in an ether solution (35 mL) containing 3.14 g of the $C_{18}$ epoxide. This was followed by dropwise addition of 0.2 mL of $BF_3$. After one hour of stirring, an additional 0.1 mL of $BF_3$ was added. Stirring was then continued for an additional three hours, and the $C_{18}$-derivatized polymer was washed in the manner described above.

To prepare an ethyl cellulose-coated continuous polymer, the dehydrated epoxy-activated continuous polymer was placed in 35 mL of acetone containing 0.5 g of ethyl cellulose. As the suspension was stirred, $BF_3$ was added. After a reaction time of 90 minutes, the polymer was washed with acetone and ether, then suspended in 10 mL of ether. Derivatization with 1,2-epoxyoctadecane was performed as described above.

$C_8$-derivatized polymers were prepared from the DTMP- and PVA-coated polymers by suspending the polymers, after dehydration, in 20 mL of toluene, and reacting the suspensions with 6.40 mL of 1,2-epoxyoctane in the presence of $BF_3$. The reaction was permitted to continue for 2 hours.

Each of these polymers was placed in a stainless steel column in the manner described above for the $C_{18}$-derivatized polymer. Table 6 lists the characteristics of each of the resulting beds. The value of C (the crosslinking concentration) for each bed was 55.9% (weight/weight).

TABLE 6

Bed Characteristics

| Bed | T (%) | Coating | Ligand Reagent | L (cm) | $V_o$ (mL) | $V_o/L$ (mL/cm) |
| --- | --- | --- | --- | --- | --- | --- |
| a | 5 | none | $C_{18}OH$ | 7.0 | 1.3 | 0.19 |
| b | 5 | none | $C_{16}C_2O^{(a)}$ | 3.4 | 1.6 | 0.48 |
| c | 5 | glucose | $C_{16}C_2O$ | 4.0 | 1.6 | 0.40 |
| d | 5 | dextran | $C_{16}C_2O$ | 3.5 | 1.2 | 0.34 |
| e | 5 | ethyl cellulose | $C_{16}C_2O$ | 3.7 | 1.1 | 0.30 |
| f | 5 | none | $C_{16}C_2O$ | 8.2 | 1.6 | 0.20 |
| g | 15 | dextran | $C_{16}C_2O$ | 14.9 | 2.5 | 0.17 |
| h | 15 | DTMP | $C_{16}C_2O$ | 4.5 | 1.3 | 0.29 |
| i | 5 | PVA | $C_{16}C_2O$ | 5.0 | 1.0 | 0.20 |
| j | 5 | DTMP | $C_{16}C_2O + C_6C_2O^{(b)}$ | 6.0 | 1.5 | 0.25 |
| k | 5 | PVA | $C_{16}C_2O + C_6C_2O$ | 4.2 | 1.5 | 0.36 |
| l[c] | 5 | PVA | $C_{16}C_2O + C_6C_2O$ | 3.0 | 1.0 | 0.33 |

[a] The symbol $C_{16}C_2O$ denotes 1,2-epoxyoctadecane.
[b] The symbol $C_6C_2O$ denotes 1,2-epoxyoctane.
[c] Bed "l" is bed "k" compressed from 4.2 cm to 3.0 cm.

Reversed-Phase Chromatography of Protein Mixture—FIGS. 7a–7l

Each of these beds was tested for reversed-phase chromatography of a sample mixture of proteins, each sample containing ribonuclease, cytochrome C, lysozyme, myoglobin and ovalbumin to a total of 150 μg of protein in a 30-μL aqueous solution. The chromatograms were developed at a flow rate of 5 mL/min at room temperature with a mobile phase consisting of a 20-mL linear gradient from 10% to 70% acetonitrile in TFA. Detection was performed at 230 nm, and the results are shown in FIGS. 7a through 7l, corresponding to beds a through of Table 6, respectively. The peaks in these chromatograms are labeled as follows:

| | |
|---|---|
| L | lysozyme |
| R | ribonuclease |
| C | cytochrome C |
| M | myoglobin |
| O | ovalbumin |

Figure 7H:
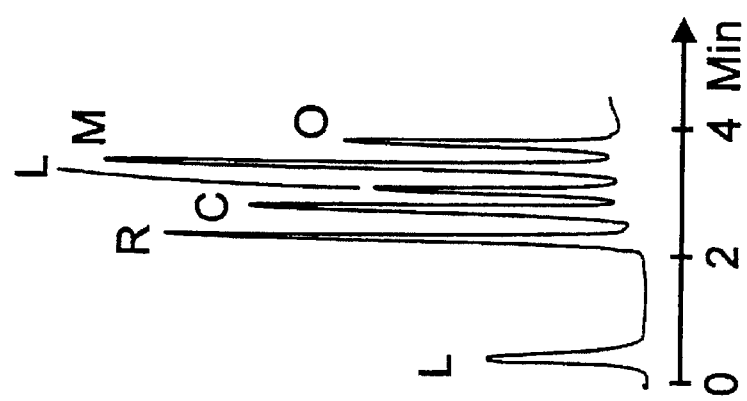
Figure 7G:
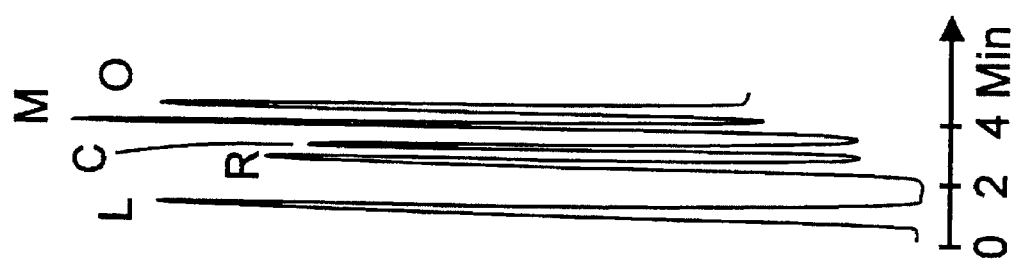
Figure 7F:
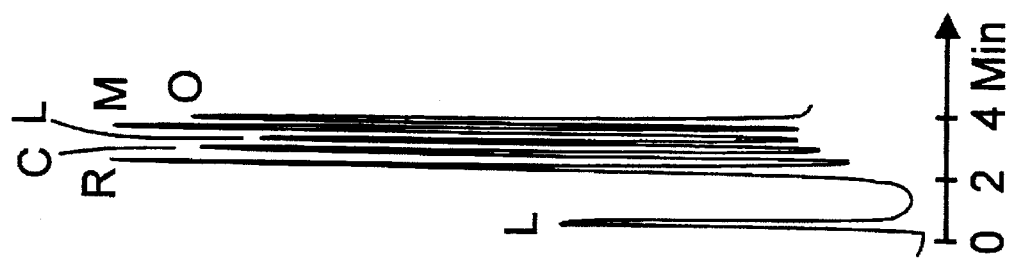
Figure 7E:
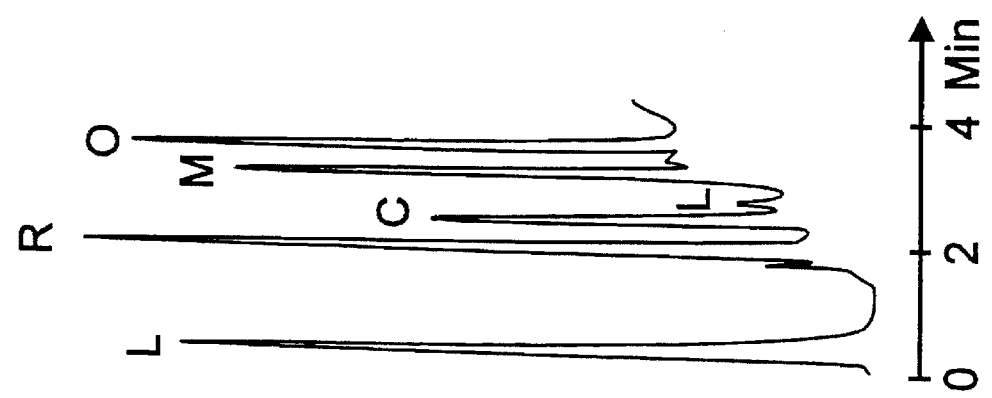

The chart speed in FIGS. 7f and 7g was half that in the other figures.

The peaks of FIG. 7a are slightly broader than those of FIGS. 7c–7l, indicating a lesser degree of non-specific interaction in coated beds as compared to non-coated. The difference in peak width between FIGS. 7a and 7b is due in part to the higher ligand density of the bed in FIG. 7b, and in part to a more hydrophilic polymer surface in the bed of FIG. 7b which resulted from the reaction between two epoxide groups as opposed to an epoxide group and a hydroxyl group.

A comparison between the chromatograms of FIGS. 7k and 7l indicates that increasing the degree of compression of the bed results in narrower peaks.

B. Reversed-Phase Chromatography of Pepsin-Digested Myoglobin—FIG. 8

Figure 8:
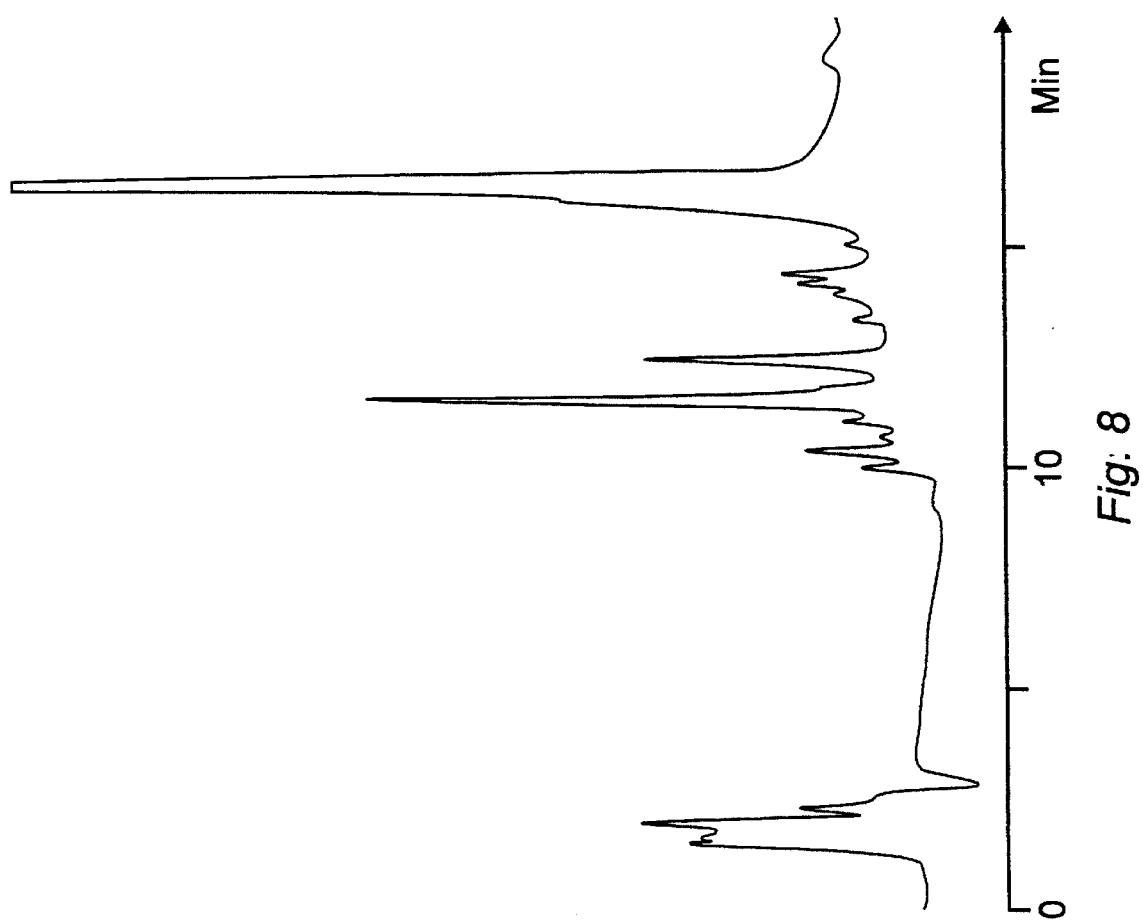
FIG. 8 is a chromatogram representing reversed-phase chromatography of pepsin-digested myoglobin using the bed used in FIG. 7k.

A reversed-phase separation of pepsin-digested myoglobin was performed bed k of Table 6, a PVA-coated bed derivatized with 1,2-epoxyoctadecane and 1,2-epoxyoctane, and the same apparatus described above in this example. The dimensions of the bed were 0.6 mm (i.d.)×4.5 cm, the flow rate was 1 mL/min, and the sample volume was 200 μL of a solution prepared by dissolving 5 mg of the digest in 1 mL of water. Solvent A was 0.1% (volume/volume) TFA in water, and solvent B was 0.1% (volume/volume) TFA in acetonitrile. The column was equilibrated with solvent A. The chromatogram was developed with an isocratic elution with solvent A for 2 minutes, followed by a gradient from 0% to 60% solvent B over 14 minutes, and finally a gradient of 60% to 100% solvent B over 4 minutes, all at room temperature. Detection was performed at 230 nm, and the results are shown in FIG. 8, which indicates that a chromatographic separation of the digest into peaks was achieved.

C. Reversed-Phase Chromatography of Self-Digested Trypsin—FIG. 9

Figure 9:
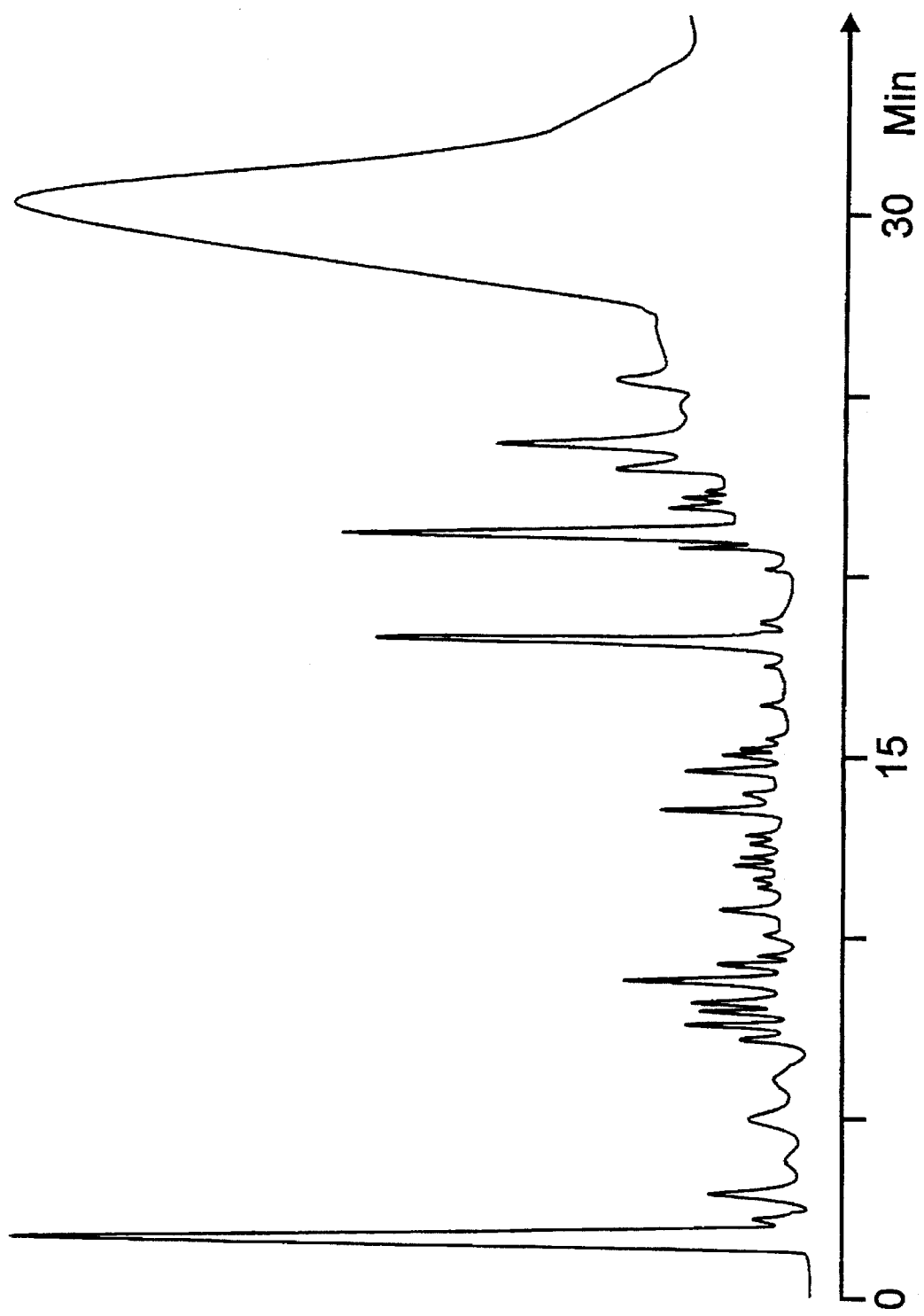
FIG. 9 is a chromatogram representing reversed phase chromatography of self-digested trypsin using the bed used in FIG. 7k.

A reversed-phase separation of self-digested trypsin was also performed on bed k of Table 6. The dimensions of the bed were 0.6 mm (i.d.)×4.4 cm. The sample was prepared by dissolving 5 mg of trypsin in 0.01M Tris-HCl at pH 7.5, and permitting the solution to stand for 5 minutes at 40° C. for self-digestion to occur. The volume of sample used for chromatographic separation was 30 μL. Solvent A was 0.1% (volume/volume) TFA in water, and solvent B was 0.1% (volume/volume) TFA in acetonitrile. The column was equilibrated with 10% solvent B in solvent A. The chromatogram was developed with a gradient elution from 10% to 37% (volume/volume) solvent B in solvent A over 23 minutes, followed by 37% to 60% over seven minutes, and finally 60% to 100% over ten minutes, all at room temperature. Detection was performed at 230 nm, and the results are shown in FIG. 9, which indicates that a chromatographic separation of the digest into peaks was achieved.

D. Influence of Temperature on Retention Times and Peak Resolution—FIGS. 10a–10d Bed k was once again used, this time however, in several separations differing in temperature. The dimensions of the bed were 0.6 mm (i.d.)×4.4 cm. The sample was BrCN-cleaved cellulase, the sample volume was 10 μL, and the flow rate was 0.7 mL/min. Solvent A was 0.1% (volume/volume) TFA in water, and solvent B was 0.1% (volume/volume) TFA in acetonitrile aqueous solution. The column was equilibrated with solvent A. The chromatogram was developed with a gradient elution from 10% to 50% (volume/volume) solvent B in solvent A over 40 minutes, with detection at 230 nm. The separations were performed at 3° C. (FIG. 10a), 14° C. (FIG. 10b), 40° C. (FIG. 10c) and 50° C. (FIG. 10d).

The results show that the resolution increases with an increase in temperature, with the highest resolution obtained when separation was performed at 40° C. The results also show that the retention times decrease with an increase in temperature, with the decrease in retention time being successively more pronounced as the size of the peptide decreases.

E. Pressure vs. Flow Rate—FIG. 11

Figure 11:
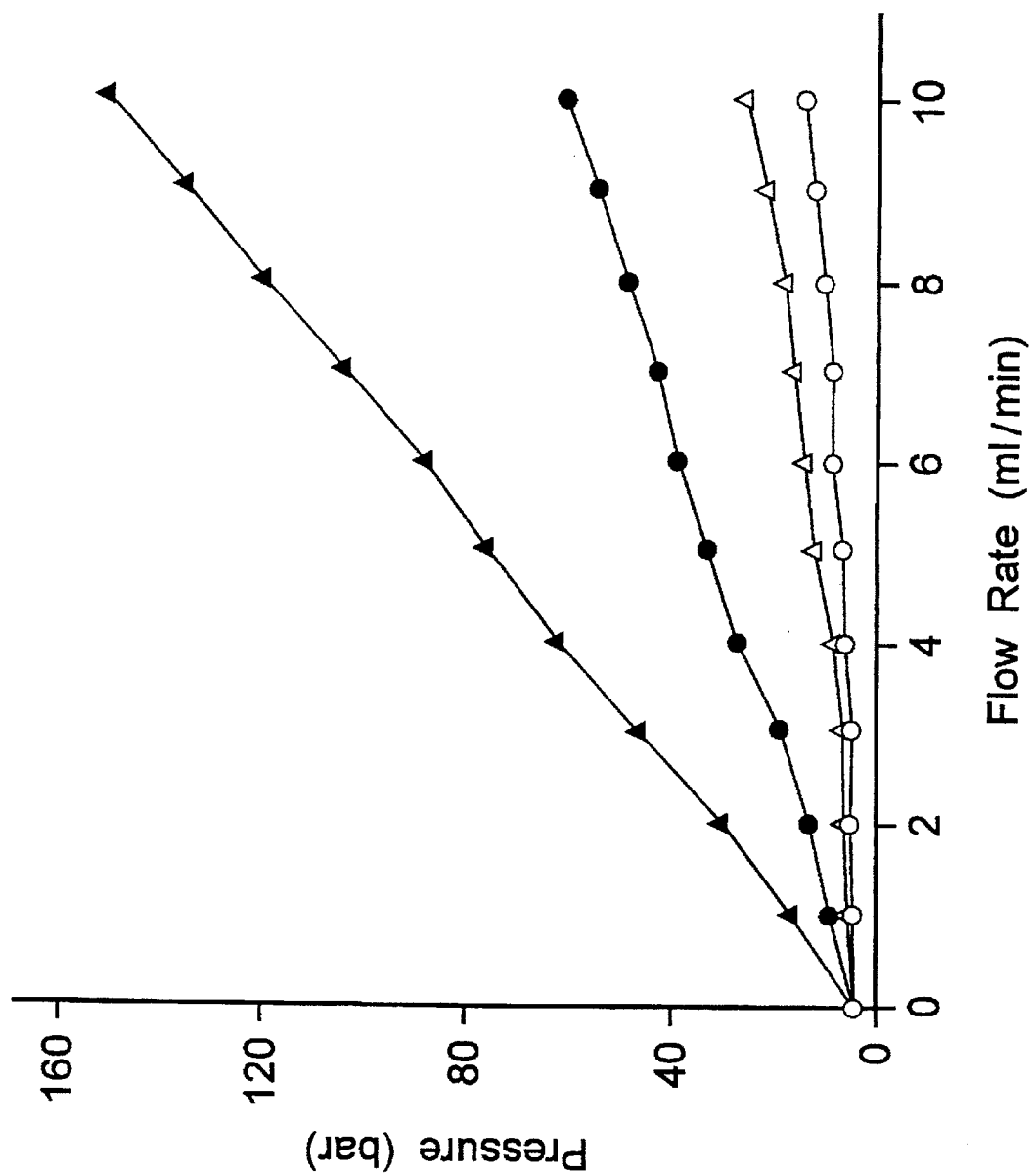
FIG. 11 is a plot of back pressure vs. flow rate for one of the beds of the present invention.

To determine the relation between pressure and flow rate, bed g of Table 6 (a dextran-coated bed derivatized with 1,2-epoxyoctadecane) was tested with the two solvents used in the preceding sections of this example. The bed dimensions were 0.6 mm×11.7 cm. The results are shown in FIG. 11, where the mobile phases were as follows:

filled triangles: 0.1% TFA in distilled water filled circles: 0.1% TFA in acetonitrile open triangles: 0.1% TFA in distilled water in the absence of the polymer but with the frit retained open circles: 0.1% TFA in acetonitrile in the absence of the polymer but with the frit retained The plot indicates a relationship which is normal for a polymer-filled column.

Figure 12A:
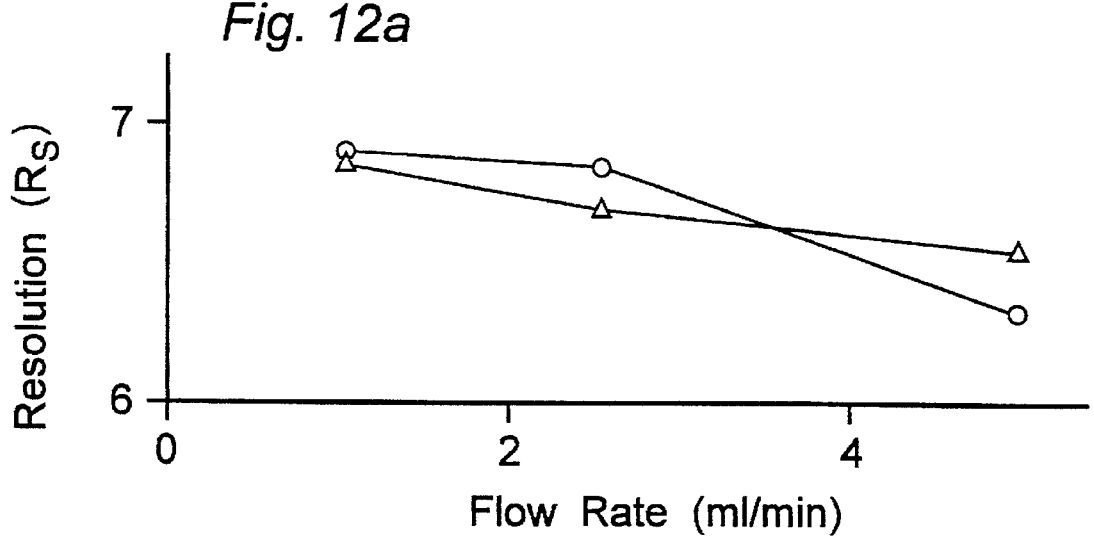
FIGS. 12a and 12b are plots of the peak resolution vs. flow rate for two beds prepared in accordance with the invention.
Figure 12B:
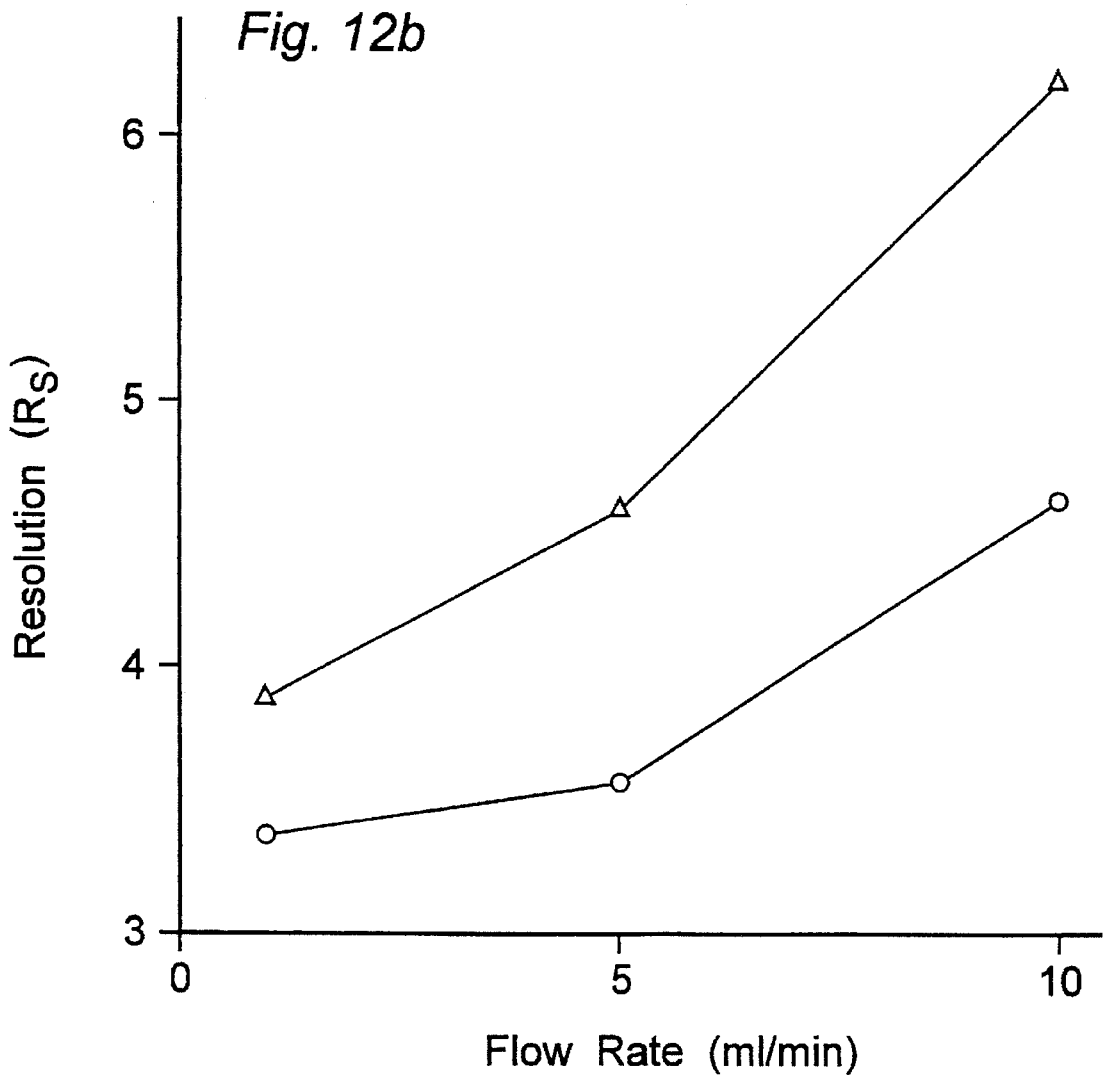

F. Resolution rs. Flow Rate—FIGS. 12a and 12b

Resolution studies were performed using beds d and g of Table 6. Bed d was dextran-coated PVA derivatized with 1,2-epoxyoctadecane at T=5%, whereas bed g was dextran-coated PVA derivatized with 1,2-epoxyoctadecane at T=15%. Two mixtures were used to study the resolution. The first was a mixture of ribonuclease and cytochrome C (represented by the circles in the plots); and the second was a mixture of myoglobin and albumin (represented by the open triangles). The resolution $R_s$ was defined by the formula $$R_s = \frac{t_2 - t_1}{0.5 \times (t_{w2} + t_{w1})}$$

where $t_2$ and $t_1$ denote the retention times of the two proteins, respectively, in the media tested, and $t_{w2}$ and $t_{w1}$ denote the peaks widths. The plots, which appear in FIGS. 12a (for bed d) and 12b for bed g, show that the resolution decreased somewhat for bed d with an increase in flow rate, but increased for bed g.

EXAMPLE 4

This example illustrates the effects of several additional variables on the performance of a packed bed prepared in accordance with the invention. This example also offers further test results obtained from HPLC separations using both reversed-phase and cation-exchange media in accordance with the invention.

A. Flow Resistance vs. Crosslinking Concentration—FIG. 13

Glass test tubes were charged with piperazine diacrylamide (PDA) and methacrylamide (MA) in differing proportions but at a total weight of 0.25 g, dissolved in 5-mL portions of 0.05M potassium phosphate, pH 6.8. The value of T was thus constant at 5% (weight/volume) among these preparations, while the value of C varied. Ammonium sulfate was added (0.25 g per 5 mL of monomer solution), followed by 50 µL of a 10% (weight/volume) aqueous solution of ammonium persulfate. Following the ammonium persulfate addition, the solutions were aerated for 2 minutes, then supplemented with 50 µL of an aqueous solution of 5% TEMED. Polymerization then proceeded at room temperature for six hours.

Figure 13:
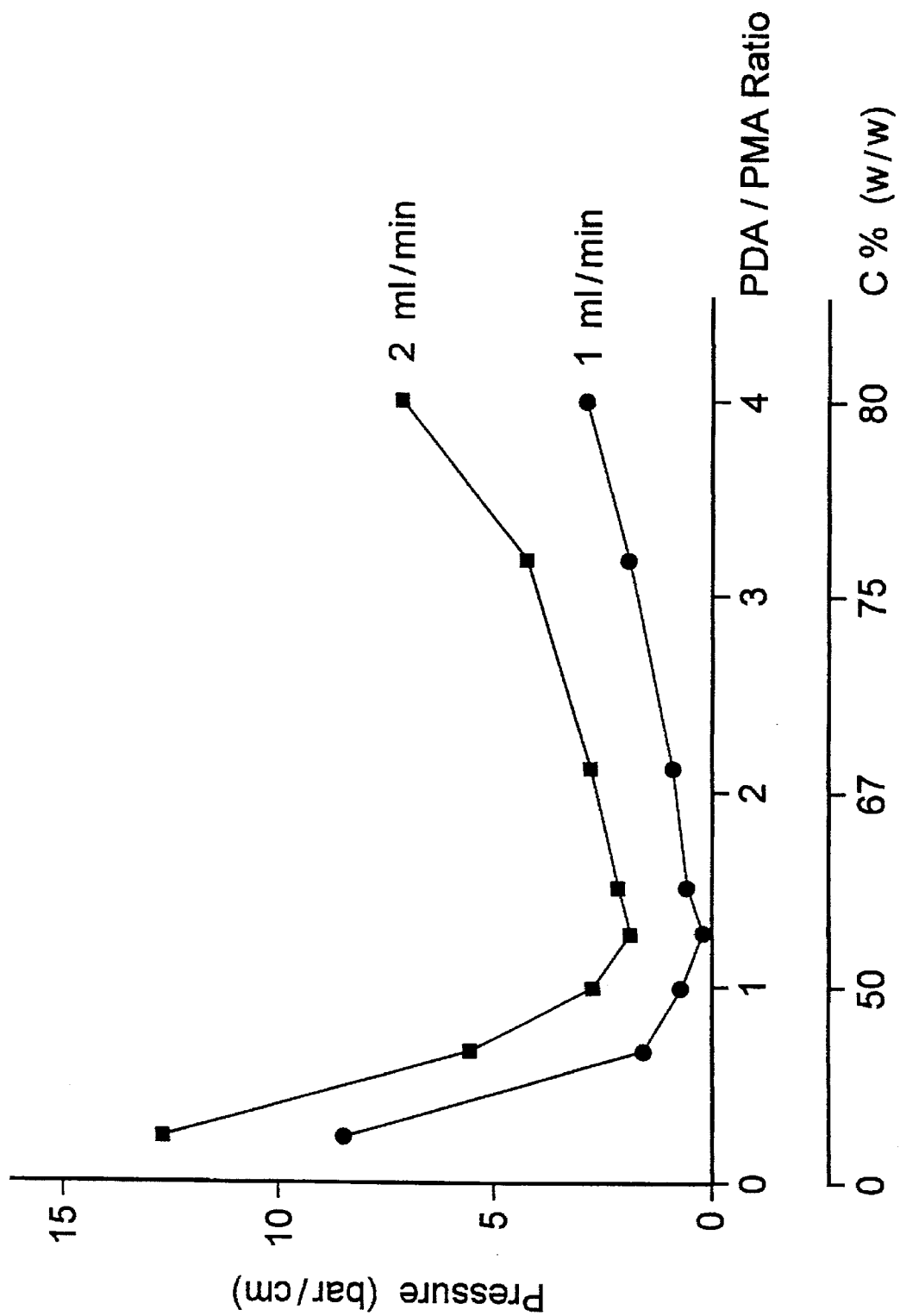
FIG. 13 is a plot of the flow resistance vs. crosslinking concentration for a bed prepared in accordance with the invention, at two flow rates.

The resulting polymer was broken into large lumps by continuous stirring, then suspended in 5 mL of distilled water and packed at a flow rate of 2 mL/min into columns measuring 0.6 mm (i.d.)×3.5 cm. Once loaded, the beds were compressed manually by pistons at the tops of the columns. Distilled water was then passed through the columns and the back pressures and flow rates observed. The back pressure on the columns was read at flow rates of 1 and 2 mL/min and plotted against C. A plot of back pressure in bar per bed height in cm is shown in FIG. 13, where the filled circles represent the flow rate of 1 mL/min and the filled squares represent the flow rate of 2 mL/min. The plot indicates that the minimum flow resistance for this bed at both flow rates was achieved with a PDA/MA weight ratio of 1.27 (C=55.9%).

B. Flow Resistance vs. Ammonium Sulfate Concentration—FIG. 14

A series of polymer beds were prepared as in Part A of this example, except that the PDA/MA ratio was held constant at 1.27 (C=55.9%) while the ammonium sulfate concentration was varied between 20 and 160 mg/mL. The back pressure was read at flow rates of 1 ml/min, 2 mL/min, 3 mL/min, 4 mL/min and 5 mL/min.

Figure 14:
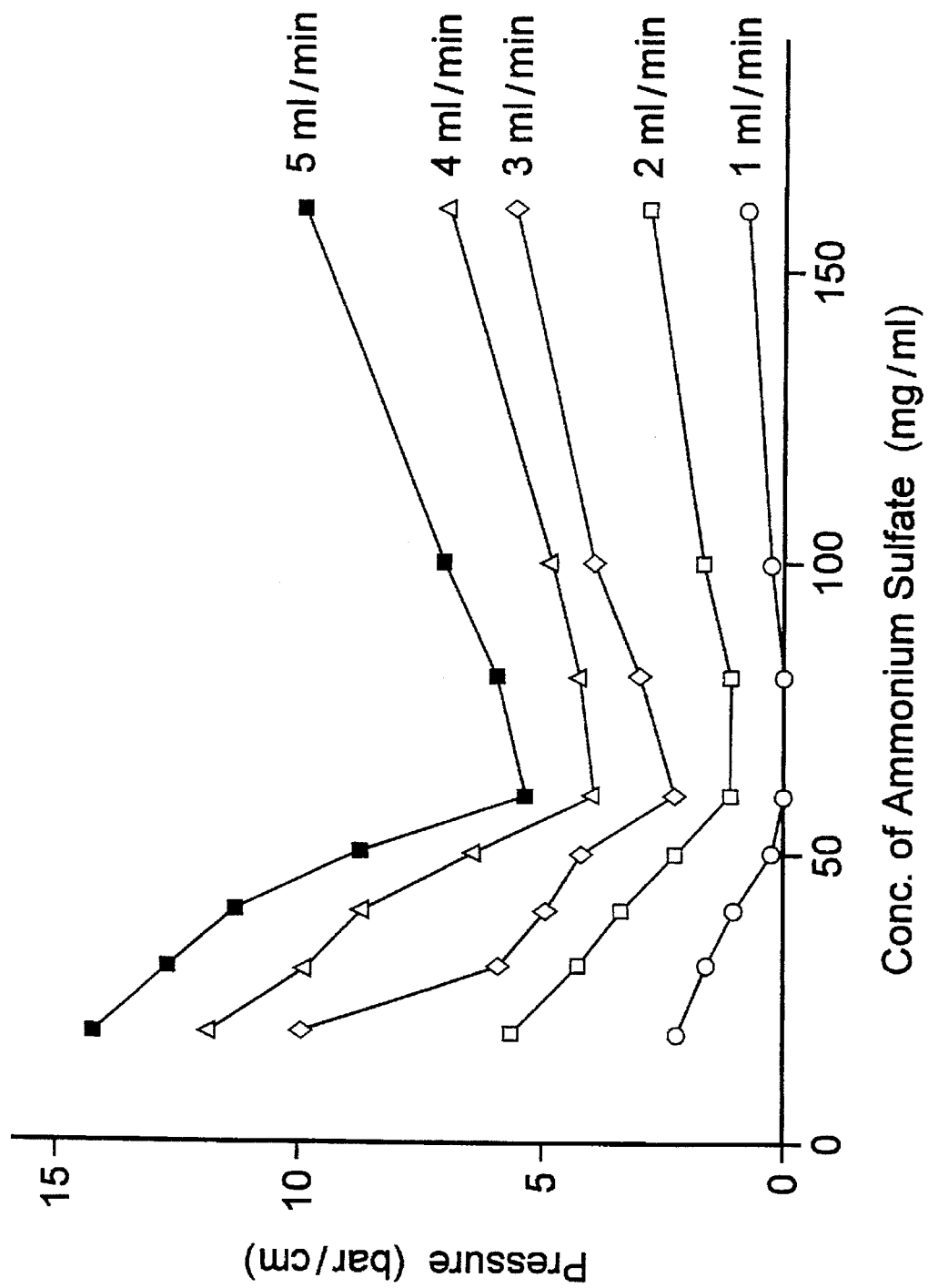
FIG. 14 is a plot of back pressure vs. the amount of salting-out salt present, for five different flow rates.

FIG. 14 is a plot of the back pressure per unit bed height vs. the ammonium sulfate concentration at each of the flow rates where the measurement was taken. The plot indicates that the minimum flow resistance for each flow rate was obtained when the concentration of ammonium sulfate was 60 mg/mL.

C. Stability Relative to Hydrolysis vs. pH—FIG. 15

A typical method of regenerating the column after use is by purging the column with a wash solution of either high or low pH. Since the amide bonds in the polymer are susceptible to hydrolysis, it is useful to know the pH values where appreciable hydrolysis begins to occur. To determine this, use is made of the fact that hydrolysis exposes free carboxylic acid groups, which give the bed the character of a cation exchanger. The degree of hydrolysis is therefore estimated by treating the bed with buffers varying in pH for various periods of time, and then determining the amount of a basic protein that adsorbs to the bed at low ionic strength.

The tests were performed with a bed having a crosslinking concentration C=55.9% and an ammonium sulfate concentration of 60 mg/mL, in a column measuring 0.6 mm (i.d.)×3 cm. Each of a series of columns loaded in this manner was equilibrated with a buffer solution ranging in pH from 1 to 12, at a flow rate of 1 mL/min. Equilibration was continued for varying periods of time ranging up to 21 days. A 10 µL volume of human hemoglobin was then injected into each column, and the columns were washed with their respective equilibration buffers for 2 minutes.

A portion of the injected hemoglobin was adsorbed by the column in each case. This adsorbed portion was eluted with a 3-mL salt gradient formed from the equilibration buffer and the same buffer containing 1M sodium chloride. The relative amounts of non-adsorbed and adsorbed hemoglobin were then determined from the measurements of peak areas detected at 280 nm.

Figure 15:
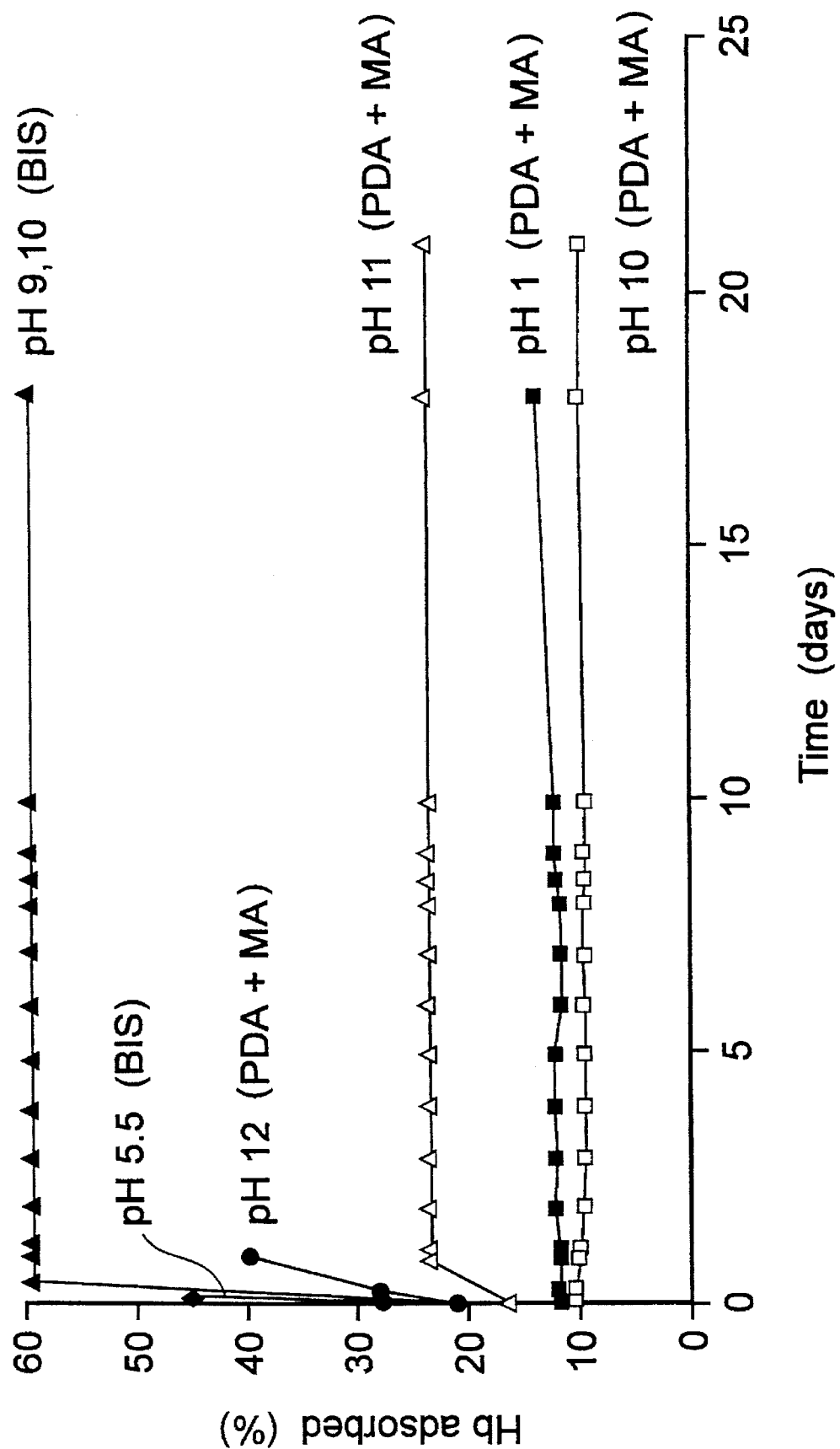
FIG. 15 is a plot demonstrating the stability of various gels prepared in accordance with the invention upon exposure to both high and low pH conditions for varying lengths of time.

The percent hemoglobin adsorbed is plotted against the wash buffer exposure time at the various pH values in FIG. 15. This figure also includes data from tests performed in beds which used BIS (N,N'-methylenebisacrylamide) in place of PDA. The various tests are represented in the Figure as follows:

open squares: PDA/MA; pH 10 filled squares: PDA/MA; pH 1 open triangles: PDA/MA; pH 11 filled circles: PDA/MA; pH 12 filled triangles: BIS/MA; pH 5.5 filled diamonds: BIS/MA; pH 9, 10

The plot shows that the PDA/MA beds are very stable relative to hydrolysis over a pH range of 1–11 for at least three weeks. At pH 12, the beds are stable for 6 hours. In addition, the PDA/MA beds are superior to the BIS-based beds in this respect.

D. Cation Exchanger: Flow Resistance vs. Flow Rate—FIG. 16

Figure 16:
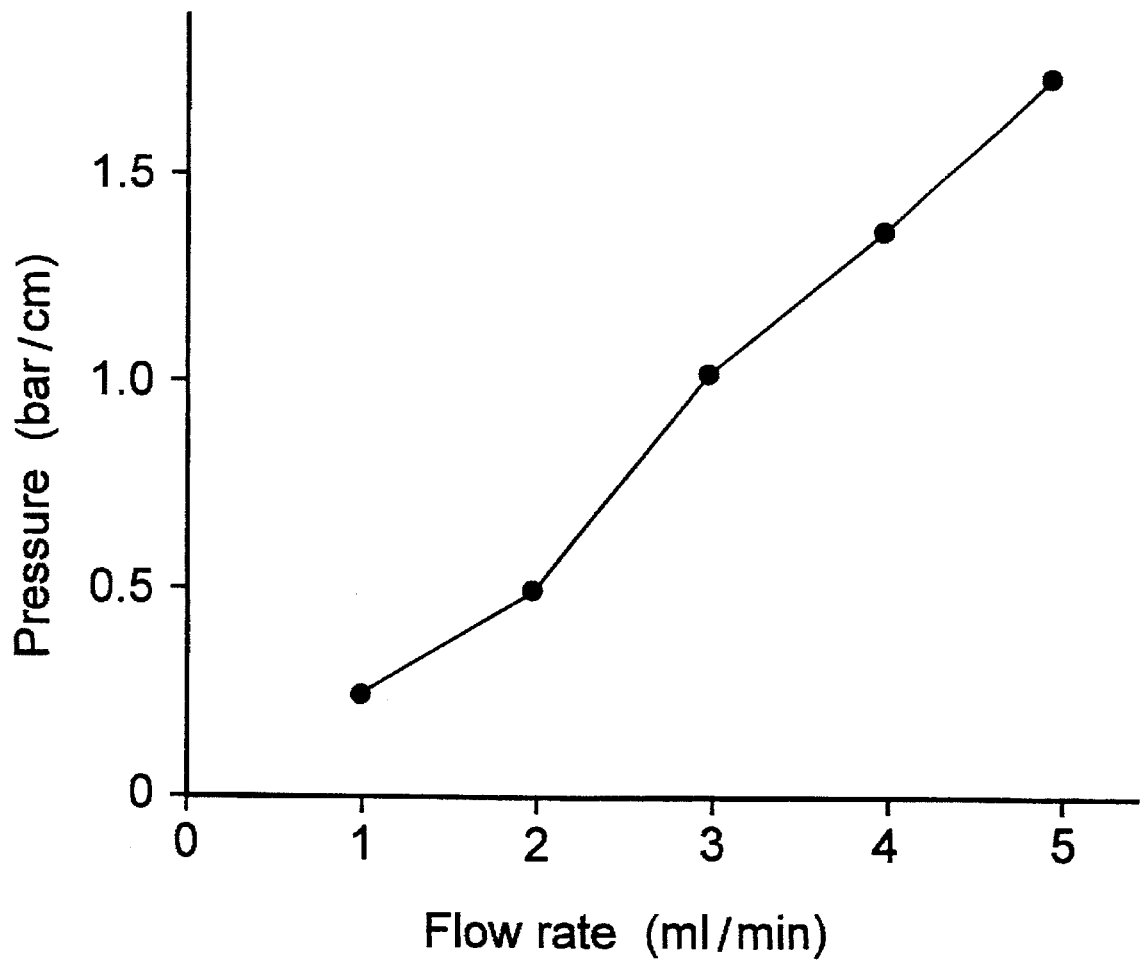
FIG. 16 is a plot of flow resistance vs. flow rate in a cation exchanger prepared in accordance with the present invention.

A cation exchanger in accordance with the present invention was synthesized by dissolving 1 g of PDA and MA combined, in a weight ratio of 1.27, 1.2 g ammonium sulfate, and 10 µL of acrylic acid in 20 mL of 0.05M potassium phosphate at pH 6.8. A 10% aqueous solution of ammonium persulfate (200 µL) was then added, the solution deaerated, and 200 µL of a 5% solution of TEMED was added. The polymer obtained was mixed with 20 mL of distilled water, and packed at a high flow rate (5 mL/min) into a column measuring 0.6 mm (i.d.)×15.5 cm. Further compression of the bed to a final height of 15.5 cm was achieved with the aid of a piston. The flow resistance of the column was determined by measuring the back pressure of the column at different flow rates in the range of 1–5 mL/min. FIG. 16 is a plot of back pressure vs. flow rate.

E. Cation Exchanger: Resolution vs. Flow Rate— FIGS. 17a–17e

A column was prepared as in Part D of this example and equilibrated with 0.01M potassium phosphate, pH 6.2. A test sample 20 µL in volume was then injected into the column, the sample containing 5–10 µL each of five proteins— ovalbumin, horse skeletal muscle myoglobin, whale myoglobin, cytochrome C and lysozyme. Elution was performed at a flow rate of 5 mL/min with 6 mL of an elution buffer in a linear gradient elution achieved by combining the equilibration buffer with the same buffer containing 0.5M sodium chloride. The experiment was repeated at flow rates of 2.5, 0.5 and 0.25 mL/min.

The chromatograms are shown in FIGS. 17a (5 mL/min), 17b (2.5 mL/min), 17c (0.5 mL/min) and 17d (0.25 mL/min), together with a blank to show the baseline (FIG. 17e ). In these chromatograms, the peaks are designated as follows:

1. ovalbumin 2. horse skeletal muscle myoglobin 3. whale myoglobin 4. cytochrome C 5. lysozyme These chromatograms show that the resolution of the proteins was unaffected by the flow rate.

F. Cation Exchanger: Separation Pattern vs. Bed Height—FIGS. 18a–18h

Figures 18A, 18B, 18C, 18D, 18E, 18F, 18G, 18H:
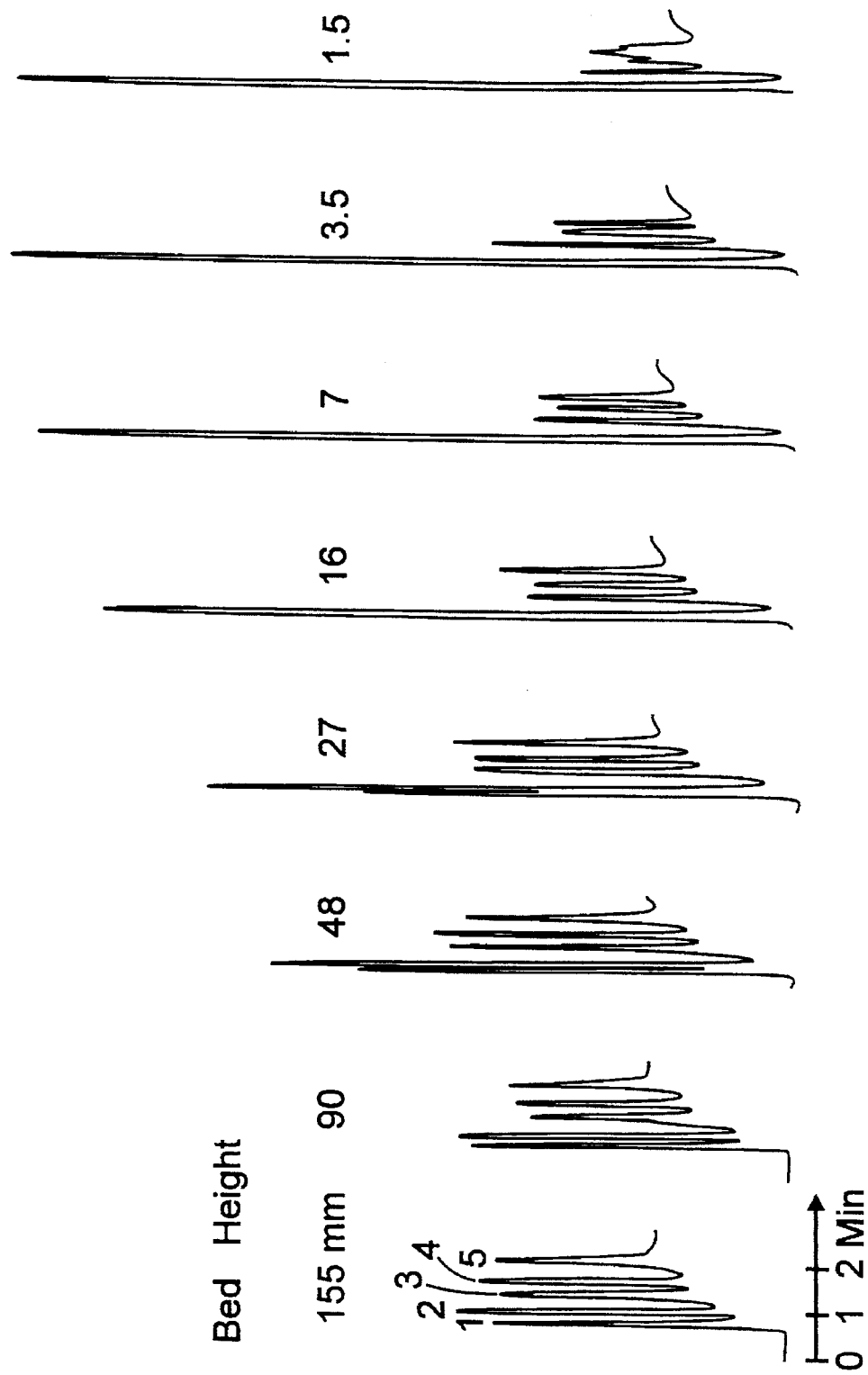
FIGS. 18a through 18f are a series of chromatograms using the same system as FIG. 17a, but varying in bed height.

The cation exchanger prepared in Part D of this example was packed into colummns of different bed heights, ranging from 0.15 to 15.5 cm. The columns were then used for the separation of the protein mixture of Part E above at a flow rate of 5 mL/min. The chromatograms are shown in FIGS. 18a–18h, as follows:

FIG. 18a: bed height 15.5 cm
FIG. 18b: bed height 9.0 cm
FIG. 18c: bed height 4.8 cm
FIG. 18d: bed height 2.7 cm
FIG. 18e: bed height 1.6 cm
FIG. 18f: bed height 0.7 cm
FIG. 18g: bed height 0.35 cm
FIG. 18h: bed height 0.15 cm The chromatograms show that the proteins in this mixture are efficiently separated on a bed as short as 2.7 cm without loss of resolution.

G. Flow Resistance rs. T—FIG. 19

Using a reversed-phase bed similar to that of Part C of this example, the flow resistance was determined as a function of the total concentration T of the monomers. In this case, however, polymerization of the polymer was performed directly in the chromatographic tube rather than in a test tube from which the polymerized polymer was then transfered to the chromatographic tube, as in the preceding parts of this example.

The tube measured 6 mm (i.d.), and the monomer solution was prepared with a crosslinking concentration C of 55.9% and an ammonium sulfate concentration of 60 mg/mL. The total monomer concentration T in the various tubes was 5%, 10%, 15%, 17.5% and 20% (weight/volume). The volume of monomer solution used was 4 mL, and polymerization was allowed to continue for 14–16 hours. After polymerization, water was pumped into each column, first at a flow rate of 1 mL/min, then at 5 mL/min and finally at 10 mL/min. This decreased the bed heights from about 13.2 cm to 1.6–8.0 cm, depending on the T value.

Figure 19:
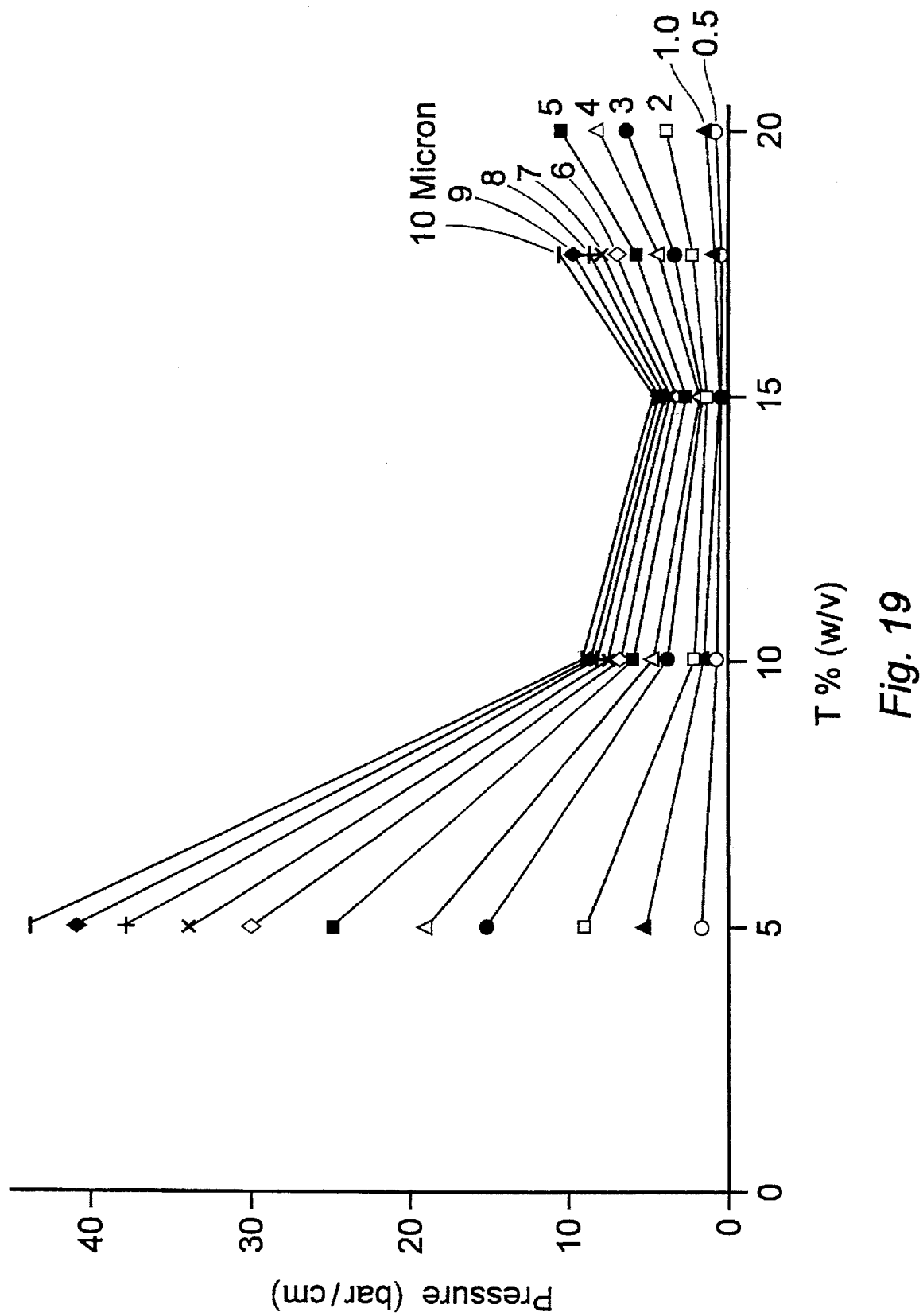
FIG. 19 is a plot of flow resistance vs. total monomer concentration for a reversed-phase bed in accordance with the invention, at a variety of different flow rates.

Distilled water was then passed through the columns, and the back pressures determined for a variety of flow rates for each T value. FIG. 19 is a plot of the pressure vs. T at different flow rates. The plotted pressure is the total pressure in the presence of the polymer minus the pressure in a column containing only water, divided by the bed height after compression. The flow rates are represented in the plot as follows:

open circles: 0.5 mL/min
filled triangles: 1.0 mL/min
open squares: 2.0 mL/min
filled circles: 3.0 mL/min
open triangles: 4.0 mL/min
filled squares: 5.0 mL/min
open diamonds: 6.0 mL/min
×: 7.0 mL/min
+: 8.0 mL/min
filled diamonds: 9.0 mL/min
−: 10.0 mL/min The data in FIG. 19 indicated that for this polymer, a total monomer concentration of T=15% (150 mg/mL) provides the least flow resistance over the range of T values tested.

H. Resolution at High Flow Rate—FIGS. 20a and 20b

To illustrate that a high resolution can still be achieved at a high flow rate, both high and low flow rate elutions were performed on reversed-phase columns prepared as in Example 3, using PDA and MA at T=15%, C=55.9%, an ammonium sulfate concentration of 60 mg/mL, and bed dimensions of 6 mm (i.d.)×14.9 cm. The bed was coated with dextran and derivatized with octadecyl groups. The test sample consisted of a mixture of ribonuclease (R), cytochrome C (C), lysozyme (L), myoglobin (M) and ovalbumin (O), at a total protein concentration of 5 mg/mL. Elution was performed as a gradient elution with 0.1% (volume/volume) TFA in water as solvent A and 0.1% (volume/volume) TFA in acetonitrile as solvent B, the gradient extending from 10% to 70% solvent B in solvent A, with a total gradient volume of 20 mL.

Figure 20A:
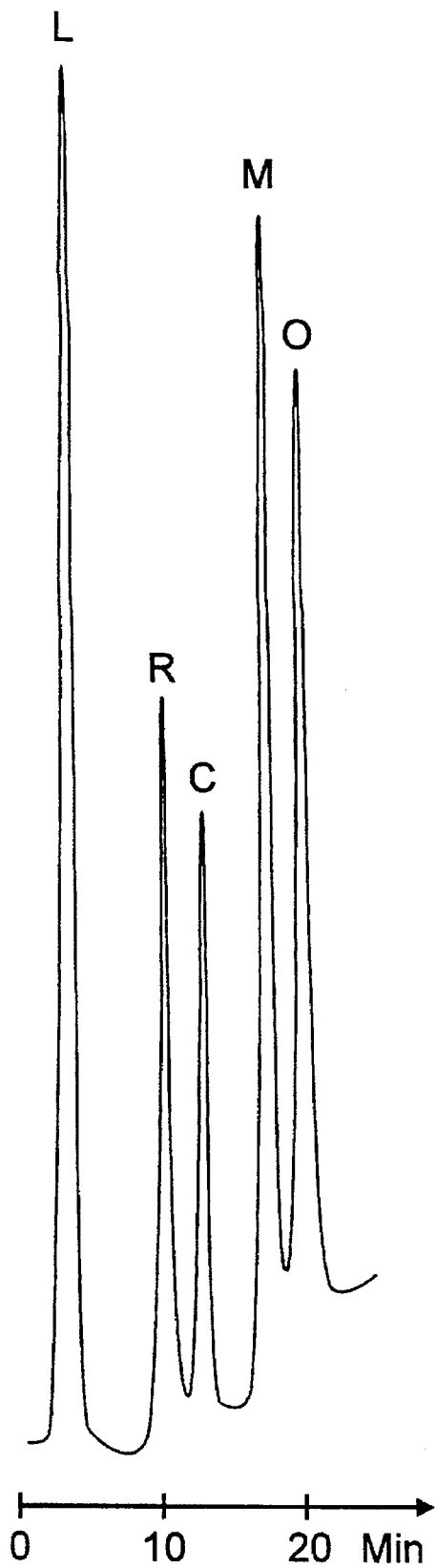
FIGS. 20a and 20b are a pair of chromatograms of a reversed-phase separation using a column in accordance with the invention, at two different flow rates.
Figure 20B:
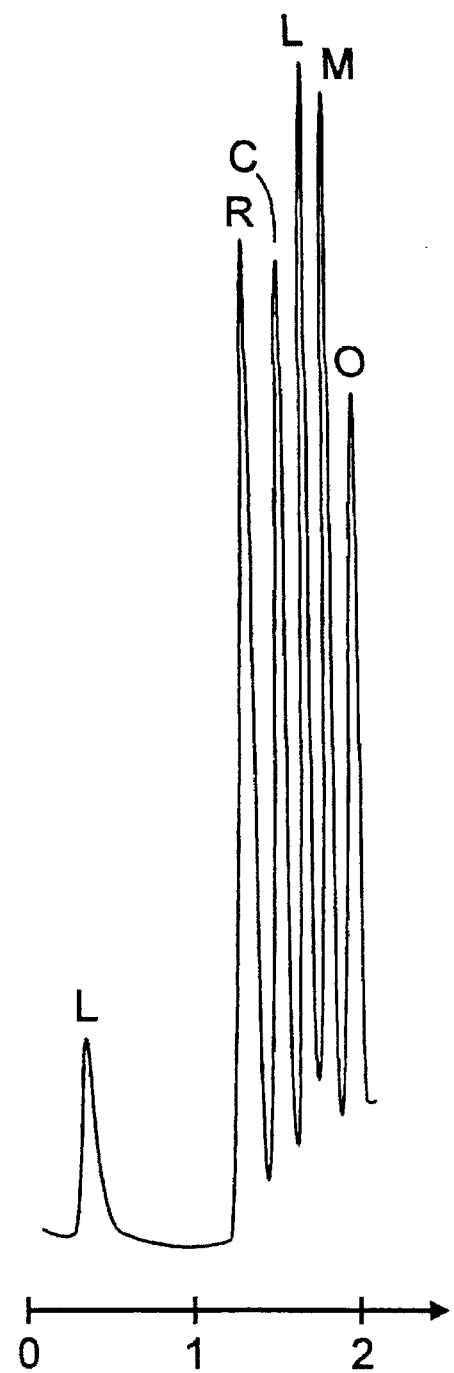

Two flow rates were used for elution—1 mL/min (6 cm/min) and 10 mL/min (60 cm/min). The chromatogram at the lower flow rate is shown in FIG. 20a, while the one at the higher flow rate is shown in FIG. 20b. The Figures show that resolution was achieved at both flow rates. The Figures also show that lysozyme elutes as a single peak at the low flow rate, as opposed to two peaks at the higher flow rate.

I. Effect of Successive Polymerizations on Bed Rigidity—FIGS. 21a and 21b

Figure 21A:
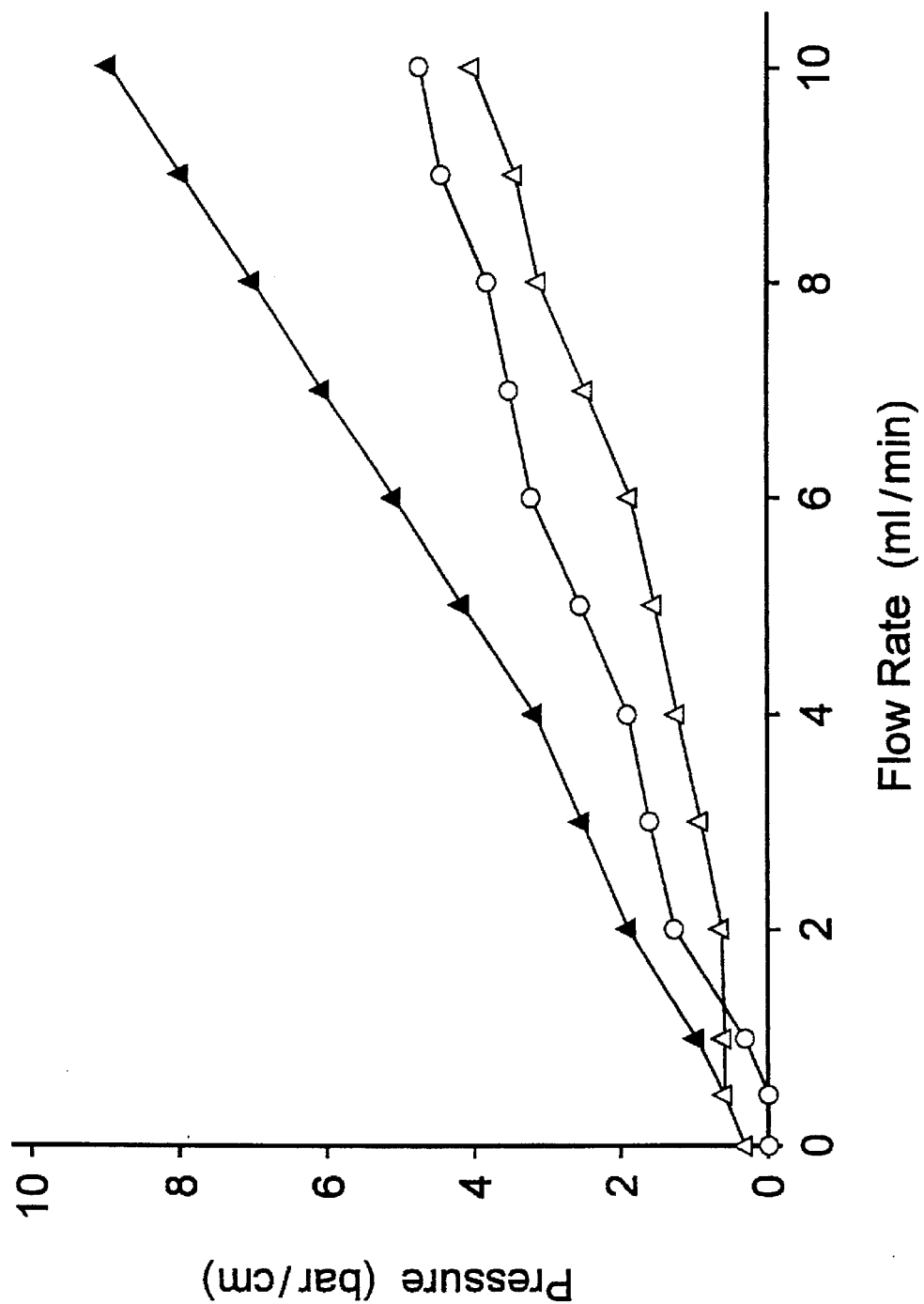
FIGS. 21a and 21b are plots of back pressure vs. flow rate at two different degrees of polymerization.
Figure 21B:
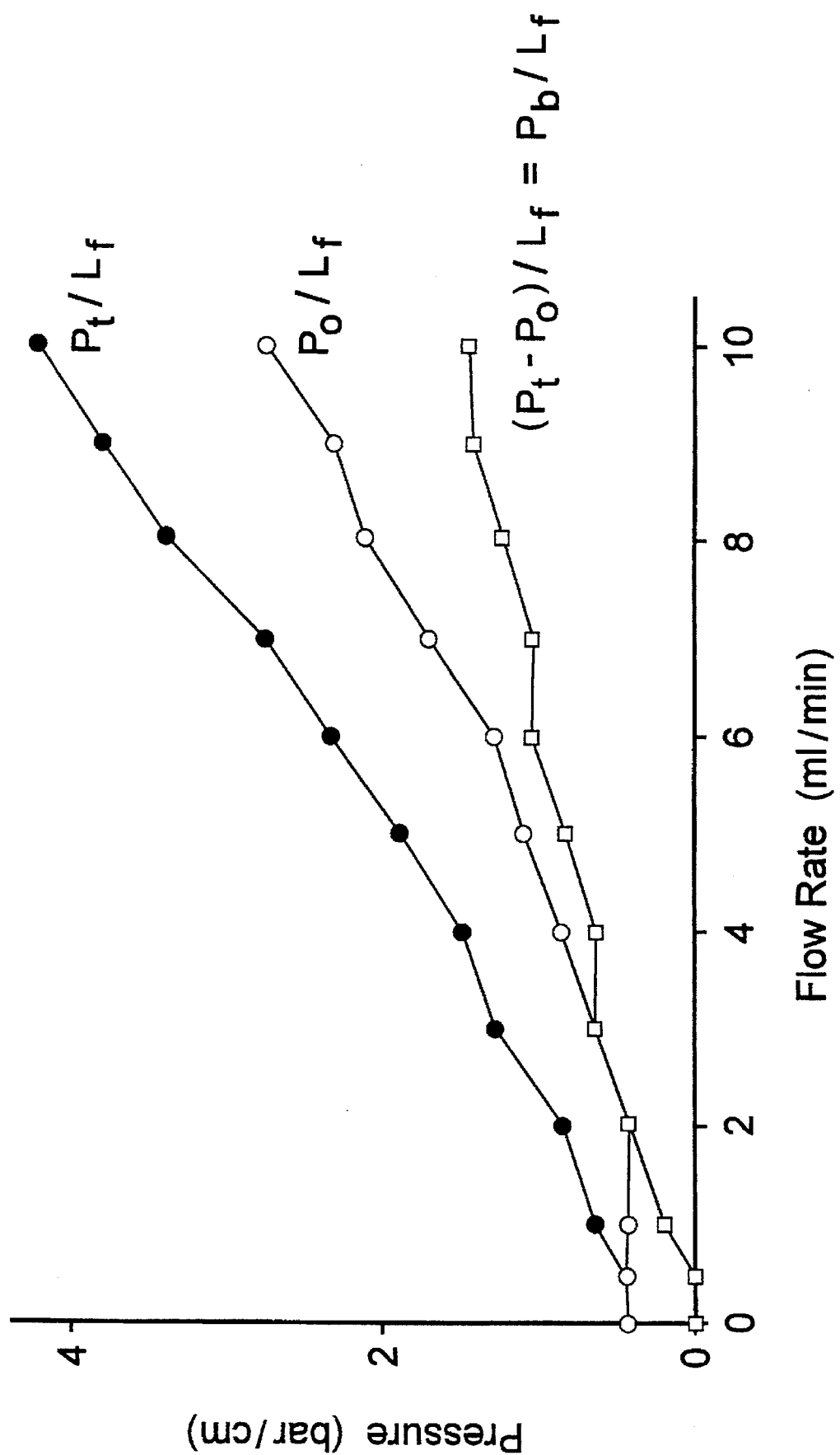

To illustrate the effect of successive polymerizations in a single bed prior to its use, the same materials were used as in Part H of this example, except that polymerization was performed directly in the chromatography tube. As in Part H, PDA and MA were used at T=15%, C=55.9%, and an ammonium sulfate concentration of 60 mg/mL. The tube diameter was 6 mm (i.d.) and the bed height was 13 cm. Once the bed was polymerized, distilled water was passed through it and the back pressure observed at various flow rates. The results are plotted in FIG. 21a, where the different measurements are designated as follows:

filled triangles: total pressure (in presence of polymer) per unit bed height vs. flow rate
open squares: total pressure (in presence of polymer) minus blank pressure (in absence of polymer), divided by the bed height, vs. flow rate
open triangles: blank pressure (in absence of polymer), divided by the bed height, vs. flow rate After these tests, further monomer solution at a monomer concentration of 50 mg/mL (T=5%) was pressed into the bed with the same syringe and allowed to polymerize for 16 hours. The polymer was then compressed at a flow rate of 10 mL/min to a bed height of 9.4 cm, and back pressure measurements were again taken. The results are plotted in FIG. 21b, where the different measurements are designated as follows:

filled circles: total pressure (in presence of polymer) per unit bed height vs. flow rate
open squares: total pressure (in presence of polymer) minus blank pressure (in absence of polymer), divided by the bed height, vs. flow rate
open circles: blank pressure (in absence of polymer), divided by the bed height, vs. flow rate A comparison of FIGS. 21a and 21b shows that the flow resistance decreased as a result of the second polymerization.

The foregoing is offered primarily for purposes of illustration. It will be readily apparent to those skilled in the art that modifications and substitutions in terms of the materials, procedures and other parameters of the system may be introduced without departing from the spirit and scope of the invention.

What is claimed is:

1. A non-water-soluble chromatographic medium comprised of a crosslinked polymer formed by polymerization of
   (a) a water-soluble monomer which is a member selected from the group consisting of vinyl, acrylic and methacrylic monomers, in an aqueous solution which further contains
   (b) a crosslinking agent in an amount such that the sum of the weight percents of the monomer and the crosslinking agent in said aqueous solution is from about 2% to about 20%, and the mole fraction of said crosslinking agent relative to the sum of said monomer and said crosslinking agent is from about 0.10 to about 0.70.

2. A non-water-soluble chromatographic medium in accordance with claim 1 in which said water-soluble monomer is a member selected from the group consisting of vinyl acetate, acrylic acid, butyl acrylate, acrylamide, methacrylamide, and glycidyl methacrylate.

3. A non-water-soluble chromatographic medium in accordance with claim 1 in which said water-soluble monomer is a member selected from the group consisting of acrylamide and methacrylamide.

4. A non-water-soluble chromatographic medium in accordance with claim 1 in which said crosslinking agent is a member selected from the group consisting of N,N'-methylenebisacrylamide and piperazine bisacrylamide.

5. A non-water-soluble chromatographic medium in accordance with claim 1 in which said water-soluble monomer is acrylamide and said crosslinking agent is piperazine bisacrylamide.

6. A non-water-soluble chromatographic medium in accordance with claim 1 in which the sum of the weight percents of the monomer and the crosslinking agent in said aqueous solution is from about 5% to about 20%.

7. A non-water-soluble chromatographic medium in accordance with claim 1 in which the mole fraction of said crosslinking agent relative to the sum of said monomer and said crosslinking agent is from about 0.15 to about 0.55.

8. A non-water-soluble chromatographic medium in accordance with claim 1 in which the mole fraction of said crosslinking agent relative to the sum of said monomer and said crosslinking agent is from about 0.25 to about 0.45.

9. A non-water-soluble chromatographic medium in accordance with claim 1 in which said aqueous solution in which said cross-linked polymer is formed further contains an inorganic salt at a concentration from about 0.15 to about 2.2 equivalents per liter.

10. A non-water-soluble chromatographic medium in accordance with claim 9 in which the concentration of said inorganic salt is from about 0.15 to about 2.5 equivalents per liter.

11. A non-water-soluble chromatographic medium in accordance with claim 9 in which the concentration of said inorganic salt is from about 0.75 to about 1.5 equivalents per liter.

12. A non-water-soluble chromatographic medium in accordance with claim 9 in which said inorganic salt is a sulfate salt.

13. A non-water-soluble chromatographic medium in accordance with claim 1 in which said aqueous solution in which said cross-linked polymer is formed further contains a water-soluble hydrophilic polymer at a concentration from about 5% to about 20% by weight.

14. A non-water-soluble chromatographic medium in accordance with claim 1 in which said crosslinked polymer is compressed subsequent to polymerization to less than about 75% of its volume.

15. A non-water-soluble chromatographic medium in accordance with claim 1 in which said crosslinked polymer is compressed subsequent to polymerization to from about 25% to about 60% of its volume.

16. A non-water-soluble chromatographic medium comprised of a crosslinked polymer formed by polymerization of acrylamide monomer and N,N'-methylenebisacrylamide crosslinking agent in an aqueous solution, in concentrations such that the sum of the weight percents of acrylamide monomer and N,N'-methylenebisacrylamide are from about 2% to about 4%, and the mole fraction of said N,N'-methylenebisacrylamide crosslinking agent relative to the sum of said acrylamide monomer and said N,N'-methylenebisacrylamide crosslinking agent is from about 0.4 to about 0.6.

17. A non-water-soluble chromatographic medium in accordance with claim 16 in which said aqueous solution further contains an inorganic salt at a concentration of from about 0.15 to about 2.2 equivalents per liter.

18. A non-water-soluble chromatographic medium in accordance with claim 17 in which said inorganic salt is a sulfate salt.

* * * * *